United States Patent
Hudkins et al.

(10) Patent No.: US 8,076,331 B2
(45) Date of Patent: Dec. 13, 2011

(54) SUBSTITUTED PYRIDAZINE DERIVATIVES

(75) Inventors: Robert L. Hudkins, Chester Springs, PA (US); Lars J. S. Knutsen, West Chester, PA (US); Catherine P. Prouty, Doylestown, PA (US); Babu G. Sundar, West Chester, PA (US); Kevin J. Wells-Knecht, Glenmoore, PA (US)

(73) Assignee: Cephalon, Inc., Frazer, PA (US)

( * ) Notice: Subject to any disclaimer, the term of this patent is extended or adjusted under 35 U.S.C. 154(b) by 21 days.

(21) Appl. No.: 12/846,112

(22) Filed: Jul. 29, 2010

(65) Prior Publication Data
US 2010/0311752 A1 Dec. 9, 2010

Related U.S. Application Data

(63) Continuation of application No. PCT/US2009/032187, filed on Jan. 28, 2009.

(60) Provisional application No. 61/062,908, filed on Jan. 30, 2008.

(51) Int. Cl.
| | | |
|---|---|---|
| *C07D 403/12* | (2006.01) | |
| *C07D 401/12* | (2006.01) | |
| *C07D 413/14* | (2006.01) | |
| *C07D 237/26* | (2006.01) | |
| *A61K 31/501* | (2006.01) | |
| *A61K 31/5355* | (2006.01) | |
| *A61K 31/502* | (2006.01) | |
| *A61P 3/04* | (2006.01) | |
| *A61P 25/28* | (2006.01) | |
| *A61P 25/18* | (2006.01) | |
| *A61P 25/04* | (2006.01) | |
| *A61P 15/00* | (2006.01) | |
| *A61P 25/06* | (2006.01) | |
| *A61P 25/24* | (2006.01) | |
| *A61P 25/08* | (2006.01) | |

(52) U.S. Cl. .......... 514/236.5; 514/252.03; 514/252.05; 514/248; 544/238; 544/114; 544/235; 544/234

(58) Field of Classification Search ............ 514/252.03, 514/252.05; 544/238
See application file for complete search history.

(56) References Cited

U.S. PATENT DOCUMENTS

2011/0028486 A1 * 2/2011 Dinnell et al. ........... 514/252.06
* cited by examiner

*Primary Examiner* — Susanna Moore
*Assistant Examiner* — Cecilia M Jaisle

(57) ABSTRACT

The present invention is directed to compounds having histamine $H_3$ antagonist activity, as well as methods of their use and preparation.

30 Claims, No Drawings

SUBSTITUTED PYRIDAZINE DERIVATIVES

CROSS-REFERENCE TO RELATED APPLICATIONS

This application is a continuation of International Application No. PCT/US2009/032187, filed Jan. 28, 2009, which claims priority to U.S. Provisional Application Ser. No. 61/062,908, filed Jan. 30, 2008. The disclosures of the aforementioned applications are incorporated herein by reference in their entireties for all purposes.

TECHNICAL FIELD

The present invention is directed to compounds having histamine $H_3$ antagonist activity, as well as methods of their use and preparation.

BACKGROUND

Histamine is a well established modulator of neuronal activity and at least four subtypes of histamine receptors have been reported in the literature—$H_1$, $H_2$, $H_3$, $H_4$. The histamine $H_3$ receptors play a key role in neurotransmission in the central nervous system. $H_3$ receptors are predominately expressed in the brain, localizing to the cerebral cortex, amygdala, hippocampus, striatum, thalamus and hypothalamus and can also be found in the periphery (skin, lung, cardiovascular system, intestine, GI tract, etc). $H_3$ receptors are also localized presynaptically on histaminergic nerve terminals and act as inhibitory autoreceptors (Alguacil and Perez-Garcia, 2003; Passani et al, 2004; Leurs at al, 2005; Celanire et al, 2005; Witkin and Nelson, 2004).

When $H_3$ receptors are activated by histamine, histamine release is inhibited. $H_3$ receptors are also involved in presynaptic regulation of the release of acetylcholine, dopamine, GABA, glutamate and serotonin (see Repka-Ramirez, 2003; Chazot and Hann, 2001; Leurs et al, 1998). The $H_3$ receptor demonstrates a high degree of constitutive or spontaneous activity (e.g., receptor is active in the absence of agonist stimulation) in vitro and in vivo, thus, ligands to the receptor can display, agonist, neutral antagonist or inverse agonist effects.

The location and function of histaminergic neurons in the CNS suggests that compounds interacting with the $H_3$ receptor may have utility in a number of therapeutic applications including narcolepsy or sleep/wake disorders, feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders and epilepsy (Leurs et al, 2005; Witkin and Nelson, 2004, Hancock and Fox 2004; Esbenshade et al. 2006). An $H_3$ antagonist/inverse agonist could be important for gastrointestinal disorders, respiratory disorders such as asthma, inflammation, and myocardial infarction.

Thus, compounds that exhibit $H_3$ activity are needed.

SUMMARY

The present invention is directed to compounds of Formula I:

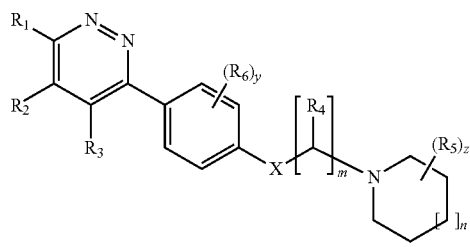

wherein
$R^1$ is H, —$OR^7$, —$SR^7$, —$SOR^7$, —$SO_2R^7$, —$NR^9R^{10}$, halogen, $C_{1-4}$ alkyl, $C_{4-10}$ cycloalkyl, $C_{1-4}$ haloalkyl, $C_{6-12}$ aryl, 5-10 membered heteroaryl, or 3-10 membered heterocycloalkyl, wherein each of said $C_{1-4}$ alkyl, $C_{4-10}$ cycloalkyl, $C_{1-4}$ haloalkyl, $C_{6-12}$ aryl, 5-10 membered heteroaryl, and 3-10 membered heterocycloalkyl is optionally substituted by 1, 2, or 3 $R^{11}$.

$R^2$ and $R^3$ are independently H or $C_{1-4}$ alkyl; or $R^2$ and $R^3$ are taken together to form a $C_{4-10}$ cycloalkyl or phenyl, wherein each of said $C_{4-10}$ cycloalkyl and phenyl is optionally substituted by 1, 2, or 3 halogen or $C_{1-4}$ alkyl;

each $R^4$ is independently H or $C_{1-4}$ alkyl or OH;
each $R^5$ is independently $C_{1-4}$ alkyl, or hydroxyalkyl;
each $R^6$ is independently halogen, $C_{1-4}$ haloalkyl, —OH, $C_{1-4}$ alkyl, —O—$C_{1-4}$ alkyl, —$NR^9R^{10}$, or CN;
$R^7$ is $C_{1-4}$ alkyl, C4-10 cycloalkyl, 5-10 membered heteroaryl, $C_{6-12}$ aryl, $C_{6-12}$ aryl$C_{1-6}$alkyl, 5-10 membered heteroarylalkyl, or a 3-10 membered heterocycloalkyl;
$R^9$ and $R^{10}$ are independently H, $C_{1-4}$ alkyl, or arylalkyl;
each $R^{11}$ is halogen, —OH, —$OC_{1-4}$ alkyl, $C_{1-4}$ alkyl, $C_{1-4}$ haloalkyl, or —CN.

X is O or S;
m is 2, 3, 4, 5, or 6;
n is 0, 1, or 2;
y is 0, 1, 2, 3, or 4;
z is 0, 1, 2, 3, or 4;
and the stereoisomers and pharmaceutically acceptable salts thereof.

Methods of making the compounds of Formula I are also described, as well as their pharmaceutical uses, in particular, as $H_3$ antagonist/inverse agonists.

DETAILED DESCRIPTION OF ILLUSTRATIVE EMBODIMENTS

The present application describes compounds according to Formula I and Formula IA, pharmaceutical compositions comprising at least one compound according to Formula I or Formula IA and optionally one or more additional therapeutic agents, and methods of treatment using the compounds according to Formula I or Formula IA both alone and in combination with one or more additional therapeutic agents, including all prodrugs, solvates, pharmaceutically acceptable salts and stereoisomers.

Preferred embodiments of the present invention are directed to compounds of Formula I:

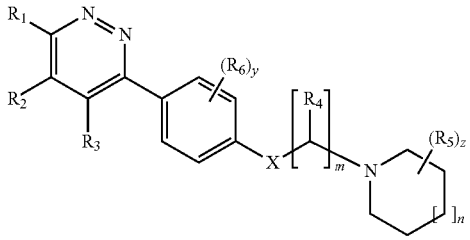

wherein
R$^1$ is H, —OR$^7$, —SR$^7$, —SOR$^7$, —SO$_2$R$^7$, —NR$^9$R$^{10}$, halogen, C$_{1-4}$ alkyl, C$_{4-10}$ cycloalkyl, C$_{1-4}$ haloalkyl, C$_{6-12}$ aryl, 5-10 membered heteroaryl, or 3-10 membered heterocycloalkyl, wherein each of said C$_{1-4}$ alkyl, C$_{4-10}$ cycloalkyl, C$_{1-4}$ haloalkyl, C$_{6-12}$ aryl, 5-10 membered heteroaryl, and 3-10 membered heterocycloalkyl is optionally substituted by 1, 2, or 3 R$^{11}$.
R$^2$ and R$^3$ are independently H or C$_{1-4}$ alkyl; or R$^2$ and R$^3$ are taken together to form a C$_{4-10}$ cycloalkyl or phenyl, wherein each of said C$_{4-10}$ cycloalkyl and phenyl is optionally substituted by 1, 2, or 3 halogen or C$_{1-4}$ alkyl;
each R$^4$ is independently H or C$_{1-4}$ alkyl or OH;
each R$^5$ is independently C$_{1-4}$ alkyl, or hydroxyalkyl;
each R$^6$ is independently halogen, C$_{1-4}$ haloalkyl, —OH, C$_{1-4}$ alkyl, —O—C$_{1-4}$ alkyl, —NR$^9$R$^{10}$, or CN;
R$^7$ is C$_{1-4}$ alkyl, C4-10 cycloalkyl, 5-10 membered heteroaryl, C$_{6-12}$ aryl, C$_{6-12}$ arylC$_{1-6}$alkyl, 5-10 membered heteroarylalkyl, or a 3-10 membered heterocycloalkyl;
R$^9$ and R$^{10}$ are independently H, C$_{1-4}$ alkyl, or arylalkyl;
each R$^{11}$ is halogen, —OH, —OC$_{1-4}$ alkyl, C$_{1-4}$ alkyl, C$_{1-4}$ haloalkyl, or —CN.
X is O or S;
m is 2, 3, 4, 5, or 6;
n is 0, 1, or 2;
y is 0, 1, 2, 3, or 4;
z is 0, 1, 2, 3, or 4;
and the stereoisomers and pharmaceutically acceptable salts thereof.

In preferred embodiments, R$^1$ is selected from the group consisting of H, —OR$^7$, —SR$^7$, —SOR$^7$, —SO$_2$R$^7$, —NR$^9$R$^{10}$, halogen, C$_{1-4}$ alkyl, C$_{1-4}$ haloalkyl, aryl and heteroaryl. In other preferred embodiments, R$^1$ is halogen, C$_{1-4}$alkyl, aryl, heteroaryl, heterocycloalkyl, or —NR$^9$R$^{10}$. In other embodiments, R$^1$ is H, halogen, or —NH$_2$. In still other embodiments, R$^1$ is chloride or fluoride. In yet other embodiments, R$^1$ is OR$^7$. Other preferred embodiments are those wherein R$^1$ is —SR$^7$, —SOR$^7$, or —SO$_2$R$^7$.

In still other embodiments, R$^1$ is H, methyl, phenyl, pyrrolidinyl, piperidinyl, morpholinyl, thiophenyl, pyridinyl, —OC$_{1-4}$alkyl, —Oaryl, —OCH$_2$aryl, —SC$_{1-4}$alkyl, —SCH$_2$aryl, —SOCH$_2$aryl, —SO$_2$CH$_2$aryl, or benzofuranyl. In other preferred embodiments, R$^1$ is H.

Certain preferred embodiments of the present invention include compounds wherein R$^5$ is C$_{1-4}$ alkyl and n is 0.

In other preferred embodiments, R$^2$ is H. In still other embodiments, R$^3$ is H.

In most preferred embodiments, R$^2$, R$^3$, R$^4$ and R$^6$ are each H.

In some preferred embodiments, R$^2$ and R$^3$ are each H. In other embodiments R$^2$ and R$^3$ are taken together to form a C$_{4-10}$ cycloalkyl. In some embodiments, R$^2$ and R$^3$ are taken together to form a phenyl.

In some preferred embodiments of the present invention, each R$^4$ is independently H or methyl. In other embodiments, R$^4$ is H.

In certain embodiments, each R$^5$ is methyl. In certain other embodiments, each R$^6$ is independently C$_{1-4}$alkyl.

Preferred embodiments of the present invention include those wherein m is 1, 2, or 3. Preferably, m is 3.

In other preferred embodiments, n is 0 or 1. Preferably n is 0.

In some embodiments, y is 0. In other embodiments, z is 1. In the most preferred embodiments, X is O.

Particularly preferred compounds of the present invention include:
3-Chloro-6-{4-[3-((R)-2-methylpyrrolidin1-yl)propoxy]phenyl}pyridazine;
3-Chloro-6-[4-(3-piperidin-1-yl-propoxy)-phenyl]pyridazine;
3-Methyl-6-{4-[3-((R)-2-methyl-pyrrolidin-1-yl)-propoxy]-phenyl}pyridazine;
3-{4-[3-((R)-2-Methyl-pyrrolidin-1-yl)-propoxy]-phenyl}-6-phenylpyridazine;
3-{4-[3-((R)-2-Methyl-pyrrolidin-1-yl)-propoxy]-phenyl}-6-pyrrolidin-1-yl-pyridazine;
4-(6-{4-[3-((R)-2-Methylpyrrolidin-1-yl)-propoxy]phenyl}pyridazin-3-yl)morpholine;
6-{4-[3-((R)-2-Methyl-pyrrolidin-1-yl)-propoxy]-phenyl}pyridazin-3-ylamine;
Methyl-(6-{4-[3-((R)-2-methyl-pyrrolidin-1-yl)-propoxy]phenyl}pyridazin-3-yl)amine;
1-(6-{4-[3-((R)-2-Methylpyrrolidin-1-yl)-propoxy]phenyl}pyridazin-3-yl)piperidin-4-ol;
3-Chloro-6-{3-methoxy-4-[3-((R)-2-methyl-pyrrolidin-1-yl)propoxy}phenyl}pyridazine;
3-Chloro-6-[3-methoxy-4-(3-piperidin-1-yl-propoxy)phenyl]pyridazine;
3-Chloro-6-[2-methyl-4-(3-piperidin-1-yl-propoxy)phenyl]pyridazine;
5-(6-Chloro-pyridazin-3-yl)-2-[3-((R)-2-methyl-pyrrolidin-1-yl)-propoxy]benzonitrile;
5-(6-Chloro-pyridazin-3-yl)-2-(3-piperidin-1-yl-propoxy)benzonitrile;
1-Chloro-4-[4-(3-piperidin-1-yl-propoxy)-phenyl]-6,7-dihydro-5H-cyclopenta[d]pyridazine;
3-{4-[3-((R)-2-Methyl-pyrrolidin-1-yl)-propoxy]phenyl}-6-thiophen-2-yl-pyridazine;
1-Chloro-4-{4-[3-((R)-2-metyl-pyrrolidin-1-yl)-propoxy]-phenyl}-6,7-dihydro-5H-cyclopenta[d]pyridazine;
3-Chloro-6-{4-[3-((R)-2-methyl-pyrrolidin-1-yl)-propoxy]-phenyl}-4,5-diaza-tricyclo[6.2.2.0*2,7*]dodeca-2(7),3,5-triene;
3-(5-Chloro-pyridin-3-yloxy)-6-{4-[3-((R)-2-methyl-pyrrolidin-1-yl)-propoxyphenyl}pyridazine;
3-Benzyloxy-6-[4-(3-piperidin-1-yl-propoxy)phenyl]pyridazine;
3-Benzyloxy-6-{4-[3-((R)-2-methyl-pyrrolidin-1-yl)-propoxy]phenyl}pyridazine;
3-Methoxy-6-{4-[3-((R)-2-methyl-pyrrolidin-1-yl-propoxy]-phenyl}pyridazine;
3-Methoxy-6-{4-3-piperidin-1-yl-propoxy)-phenyl}pyridazine;
3-Isopropoxy-6-{4-[3-((R)-2-methyl-pyrrolidin-1-yl)-propoxy]phenylpyridazine;
3-Phenoxy-6-[4-(3-piperidin-1-yl-propoxy)phenyl]pyridazine;
3-(4-Fluoro-benzyloxy)-6-{4-[3-((R)-2methyl-pyrrolidin-1-yl)-propoxy]phenyl}pyridazine;

3-{4-[3-((R)-2-Methyl-pyrrolidin-1-yl)-propoxy]-phenyl}-6-(4-trifluoromethyl-benzyloxy)pyridazine;
Ethyl-(6-{4-[3-((R)-2-methyl-pyrrolidin-1-yl)-propoxy]-phenyl}pyridazin-3-yl)amine;
Benzyl-(6-{4-[3-((R)-2-methyl-pyrrolidin-1-yl)-propoxy]-phenyl}-pyridazin-3-yl)amine;
3-{4-[3-((R)-2-Methyl-pyrrolidin-1-yl-propoxy]-phenyl}-6-methylsulfanylpyridazine;
3-Methylsulfanyl-6-[4-(3-piperidin-1-yl-propoxy)phenyl] pyridazine;
1-{4-[3-((R)-2-Methyl-pyrrolodin-1-yl)-propoxy]-phenyl}-4-methylsulfanyl-6,7-dihydro-5H-cyclopenta[d]pyridazine;
3-Benzylsulfanyl-6-{4-[3-((R)-2-methyl-pyrrolidin-1-yl)-propoxy]phenyl}pyridazine;
3-Benzylsulfanyl-6-[4-(3-piperidin-1-yl-propoxy)-phenyl] pyridazine;
3-{4-[3-((R)-2-Methyl-pyrrolidin-1-yl)-propoxy]-phenyl}-6-phenylmethanesulfinyl-pyridazine;
3-Phenylmethanesulfinyl-6-[4-(3-piperidin-1-yl-propoxy) phenyl]pyridazine;
3-{4-[3-((R)-2-Methyl-pyrrolidin-1-yl)-propoxy]-phenyl}-6-phenylmethanesulfonyl-pyridazine;
3-Phenylmethanesulfonyl-6-[4-(3-piperidin-1-yl-propoxy) phenyl]pyridazine;
1-Methoxy-4-{4-[3-((R)-2-methylpyrrolidin-1-yl)-propoxy]-phenyl}6,7-dihydro-5H-cyclopenta[d]pyridazine;
1-Methoxy-4-{4-[3-((R)-2-methyl-pyrrolidin-1-yl-propoxy]-phenyl}phthalazine;
3-Benzofuran-2-yl-6-{4-[3-((R)-2-methyl-pyrrolidin-1-yl)-propoxy]-phenyl}pyridazine;
1-Benzylsulfanyl-4-{4-[3-((R)-2-methyl-pyrrolidin-1-yl) prop oxy]-phenyl}-6,7-dihydro-5H-cyclopenta[d]pyridazine;
3-Chloro-6-{4-[(S)-2-methyl-3-((R)-2-methylpyrrolidin-1-yl)-propoxy]phenyl}pyridazine;
3-Chloro-6-{4-[(S)-2-methyl-3-(2-methylpiperidin-1-yl) propoxy]-phenyl}pyridazine; and
6-{4-[3-((R)-2-methyl-pyrrolidin-1-yl)propoxy] phenyl}pyridazine;
and the pharmaceutically acceptable salts thereof.

Also within the scope of the invention are pharmaceutical compositions comprising at least one compounds of Formula I and at least one pharmaceutically acceptable carrier or diluent. Other embodiments of the invention include pharmaceutical compositions further comprising at least one additional therapeutic agent.

Another embodiment of the present invention is directed to compounds of Formula IA:

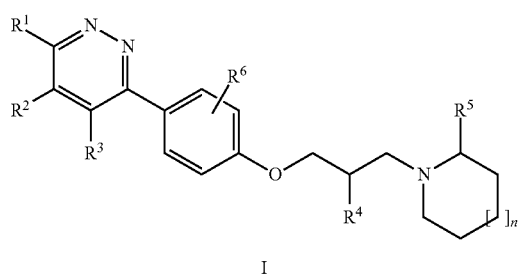

IA

I wherein
$R^1$ is selected from the group consisting of —$OR^7$, —$SR^7$, —$SOR^7$, —$SO_2R^7$, —$OSO_2R^7$, —$OC_2R^7$, —$OC(O)R^7$, —$OP(O)R^7R^8$, —$NR^9R^{10}$, halogen, $C_{1-4}$ alkyl, $C_{1-4}$ haloalkyl, aryl and heteroaryl;

$R^2$ and $R^3$ are independently selected from the group consisting of H and $C_{1-4}$ alkyl, wherein when $R^2$ and $R^3$ are both $C_{1-4}$ alkyl they may be taken together to form a 4 to 10 membered mono- or bi-cyclic ring;

$R^4$ is selected from the group consisting of H and $C_{1-4}$ alkyl;

$R^5$ is selected from the group consisting of H and $C_{1-4}$ alkyl;

$R^6$ is selected from the group consisting of H, $C_{1-4}$ alkyl, —O—$C_{1-4}$ alkyl and CN;

$R^7$ is selected from the group consisting of $C_{1-4}$ alkyl, arylalkyl and heteroarylalkyl;

$R^8$ is selected from the group consisting of H and $C_{1-4}$ alkyl;

$R^9$ and $R^{10}$ are independently selected from the group consisting of H, $C_{1-4}$ alkyl, $C_{1-4}$ alkyl wherein one C atom has been replaced by a heteroatom selected from the group consisting of O, S and N and arylalkyl, wherein when $R^9$ and $R^{10}$ are both $C_{1-4}$ alkyl or one of $R^9$ and $R^{10}$ is a $C_{1-4}$ alkyl and the other is a $C_{1-4}$ alkyl wherein one C atom has been replaced by a heteroatom selected from the group consisting of O, S and N they may be taken together to form a 4 to 7 membered heterocycle; and n is 0 or 1.

In preferred embodiments, $R^1$ is selected from the group consisting of —$OR^7$, —$SR^7$, —$SOR^7$, —$SO_2R^7$, —$NR^9R^{10}$, halogen, $C_{1-4}$ alkyl, $C_{1-4}$ haloalkyl, aryl and heteroaryl. In other embodiments $R^5$ is $C_{1-4}$ alkyl; and n is 0. In still other preferred embodiments, $R^2$, $R^3$, $R^4$ and $R^6$ are H.

Also within the scope of the invention are pharmaceutical compositions comprising at least one compounds of Formula IA and at least one pharmaceutically acceptable carrier or diluent. Other embodiments of the invention include pharmaceutical compositions further comprising at least one additional therapeutic agent.

DEFINITIONS

As employed above and throughout the disclosure, the following terms, unless otherwise indicated, shall be understood to have the following meanings.

As used herein, the term "about" refers to a range of values from ±10% of a specified value. For example, the phrase "about 50" includes ±10% of 50, or from 45 to 55. The phrase "from about 10 to 100" includes ±10% of 10 and ±10% of 100, or from 9 to 110.

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1 to 2, 1 to 3, 1 to 4, 1 to 5, 2 to 3, 2 to 4, 2 to 5, 2 to 6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, "substituted" refers to any one or more hydrogen atoms on the indicated atom is replaced with a selected group referred to herein as a "substituent", provided that the substituted atom's valency is not exceeded, and that the substitution results in a stable compound. A substituted group has 1 to 5, preferably 1 to 3, and more preferably 1 independently selected substituents. Preferred substituents include, but are not limited to F, Cl, Br, I, OH, OR, $NH_2$, NHR, $NR_2$, NHOH, $NO_2$, CN, $CF_3$, $CF_2CF_3$, $C_1$-$C_6$ alkyl, $C_2$-$C_6$ alkenyl, $C_2$-$C_6$ alkynyl, $C_1$-$C_6$ alkoxy, $C_3$-$C_7$ cycloalkyl, heterocyclyl, $C_6$-$C_{10}$ aryl, heteroaryl, arylalkyl, =O, C(=O)R, COOH, $CO_2R$, O—C(=O)R, C(=O)NRR', NRC(=O)R', $NRCO_2R'$, OC(=O)NRR', —NRC(=O)NRR', —NRC(=S)NRR', and —$SO_2NRR'$, wherein R and R' are each independently hydrogen, $C_1$-$C_6$ alkyl, or $C_6$-$C_{10}$ aryl.

As used herein, the term "alkyl" refers to a straight-chain or branched alkyl group having 1 to 8 carbon atoms, preferably from 1 to 6, with 1 to 3 more preferred. Exemplary alkyl groups include methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms. Alkyl groups may be optionally substituted.

As used herein, the term "haloalkyl" refers to a straight-chain or branched alkyl group having 1 to 8 carbon atoms, preferably from 1 to 6, with 1 to 3 more preferred, wherein at least one hydrogen atom has been replaced by a halogen atom. A designation such as "$C_1$-$C_4$ haloalkyl" refers to an haloalkyl radical containing from 1 to 4 carbon atoms. Examples of preferred haloalkyl radicals include —$CH_2F$, —CHF, and —$CF_3$.

As used herein, the term "alkenyl" refers to a straight chain, or branched hydrocarbon chains of 2 to 8 carbon atoms having at least one carbon-carbon double bond. A designation "$C_2$-$C_8$ alkenyl" refers to an alkenyl radical containing from 2 to 8 carbon atoms. Examples of alkenyl groups include ethenyl, propenyl, isopropenyl, 2,4-pentadienyl, etc. Alkenyl groups may be optionally substituted.

As used herein, the term "alkynyl" refers to a straight chain, or branched hydrocarbon chains of 2 to 8 carbon atoms having at least one carbon-carbon triple bond. A designation "$C_2$-$C_8$ alkynyl" refers to an alkynyl radical containing from 2 to 8 carbon atoms. Examples include ethynyl, propynyl, isopropynyl, 3,5-hexadiynyl, etc. Alkynyl groups may be optionally substituted.

As used herein, the term "cycloalkyl" refers to a saturated or partially saturated mono- or bicyclic alkyl ring system containing 3 to 10 carbon atoms. Certain embodiments contain 3 to 6 carbon atoms, preferably 3 or 4 carbon atoms, and other embodiments contain 5 or 6 carbon atoms. A designation such as "$C_5$-$C_7$ cycloalkyl" refers to a cycloalkyl radical containing from 5 to 7 ring carbon atoms. Examples of cycloalkyl groups include such groups as cyclopropyl, cyclobutyl, cyclopentyl, cyclohexyl, cycloheptyl, cyclooctyl, pinenyl, pinanyl, and adamantanyl. Cycloalkyl groups may be optionally substituted.

As used herein, the term "aryl" refers to a substituted or unsubstituted, mono- or bicyclic hydrocarbon aromatic ring system having 6 to 12 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene. Aryl groups may be optionally substituted.

As used herein, the terms "heterocycle", "heterocyclic" or "heterocyclyl" refer to a substituted or unsubstituted carbocyclic group in which one or more ring carbon atoms are replaced by at least one hetero atom such as —O—, —N—, or —S—. Certain embodiments include 4 to 9 membered rings preferably 3 to 7 membered rings, and other embodiments include 5 or 6 membered rings. The nitrogen and sulfur heteroatoms may be optionally oxidized, and the nitrogen may be optionally substituted in non-aromatic rings. Heterocycles are intended to include heteroaryl and heterocycloalkyl groups. Heterocyclic groups may be optionally substituted.

As used herein, the term "heteroaryl" refers to an aromatic group containing 5 to 10 ring carbon atoms in which one or more ring carbon atoms are replaced by at least one hetero atom such as —O—, —N—, or —S—. Certain embodiments include 5 or 6 membered rings. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, picolinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene. Heteroaryl groups may be optionally substituted. In certain preferred embodiments, heteroaryl is pyridinyl, more preferably pyridine-2-yl, or thienyl As used herein, the term "heterocycloalkyl" refers to a cycloalkyl group in which one or more ring carbon atoms are replaced by at least one hetero atom such as —O—, —N—, or —S—. Certain embodiments include 4 to 9 membered rings and 3 to 10 membered rings, preferably 3 to 7, more preferably 3 to 6 membered rings, and other embodiments include 5 or 6 membered rings. Examples of heterocycloalkyl groups include pyrrolidinyl, pyrrolinyl, imidazolidinyl, imidazolinyl, pyrazolinyl, pyrazolidinyl, pyrazalinyl, piperidinyl, piperazinyl, hexahydropyrimidinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl, preferably pyrrolidinyl, morpholinyl, piperidinyl, orazapanyl, more preferably pyrrolidinyl or piperidinyl. Heterocycloalkyl groups may be optionally substituted.

As used herein, the term "arylalkyl" refers to an alkyl group that is substituted with an aryl group. Examples of arylalkyl groups include, but are not limited to, benzyl, bromobenzyl, phenethyl, benzhydryl, diphenylmethyl, triphenylmethyl, diphenylethyl, naphthylmethyl, etc. preferably benzyl. Arylalkyl groups may be optionally substituted.

As used herein, the term "heteroarylalkyl" refers to an alkyl group that is substituted with a heteroaryl group. Heteroarylalkyl groups may be optionally substituted.

As used herein, the term "amino acid" refers to a group containing both an amino group and a carboxyl group. Embodiments of amino acids include α-amino, β-amino, γ-amino acids. The α-amino acids have a general formula HOOC—CH(side chain)-$NH_2$. The amino acids can be in their D, L or racemic configurations. Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. *Biochemistry*, $2^{nd}$ ed.; Worth Publishers: New York, 1975; 71-77, the disclosure of which is incorporated herein by reference. Non-naturally occurring amino acids also include α-amino acids wherein the side chains are replaced with synthetic derivatives. In certain embodiments, substituent groups for the compounds of the present invention include the residue of an amino acid after removal of the hydroxyl moiety of the carboxyl group thereof; i.e., groups of formula —C(=O)CH (side chain)-NH$_2$. Representative side chains of naturally occurring and non-naturally occurring α-amino acids include are shown below in Table A.

TABLE A

H
CH$_3$—
HO—CH$_2$—
C$_6$H$_5$—CH$_2$—
HO—C$_6$H$_4$—CH$_2$

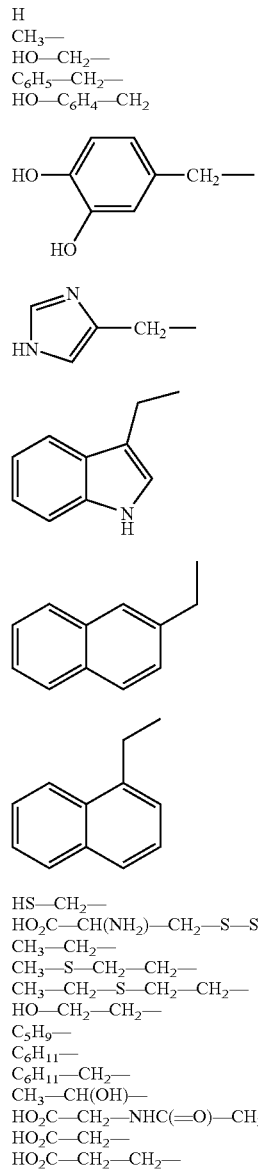

HS—CH$_2$—
HO$_2$C—CH(NH$_2$)—CH$_2$—S—S—CH$_2$—
CH$_3$—CH$_2$—
CH$_3$—S—CH$_2$—CH$_2$—
CH$_3$—CH$_2$—S—CH$_2$—CH$_2$—
HO—CH$_2$—CH$_2$—
C$_5$H$_9$—
C$_6$H$_{11}$—
C$_6$H$_{11}$—CH$_2$—
CH$_3$—CH(OH)—
HO$_2$C—CH$_2$—NHC(=O)—CH$_2$—
HO$_2$C—CH$_2$—
HO$_2$C—CH$_2$—CH$_2$—

TABLE A-continued

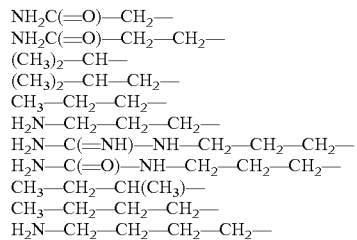

NH$_2$C(=O)—CH$_2$—
NH$_2$C(=O)—CH$_2$—CH$_2$—
(CH$_3$)$_2$—CH—
(CH$_3$)$_2$—CH—CH$_2$—
CH$_3$—CH$_2$—CH$_2$—
H$_2$N—CH$_2$—CH$_2$—CH$_2$—
H$_2$N—C(=NH)—NH—CH$_2$—CH$_2$—CH$_2$—
H$_2$N—C(=O)—NH—CH$_2$—CH$_2$—CH$_2$—
CH$_3$—CH$_2$—CH(CH$_3$)—
CH$_3$—CH$_2$—CH$_2$—CH$_2$—
H$_2$N—CH$_2$—CH$_2$—CH$_2$—CH$_2$—

As used herein, the term "subject" or "patient" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

The term "pharmaceutically acceptable excipient," as used herein, includes any and all solvents, dispersion media, coatings, antibacterial and antifungal agents, isotonic and absorption delaying agents and the like, acceptable for pharmaceutical use, for example, those that have been accorded Generally Regarded as Safe (GRAS) status by the U.S. Food and Drug Administration. The use of such media and agents for pharmaceutical active substances is well known in the art, such as in *Remington: The Science and Practice of Pharmacy*, $20^{th}$ ed.; Gennaro, A. R., Ed.; Lippincott Williams & Wilkins: Philadelphia, Pa., 2000. Except insofar as any conventional media or agent is incompatible with the active ingredient, its use in the therapeutic compositions is contemplated. Supplementary active ingredients can also be incorporated into the compositions.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

As used herein, "prodrug" refers to compounds specifically designed to maximize the amount of active species that reaches the desired site of reaction, which are of themselves typically inactive or minimally active for the activity desired, but through biotransformation are converted into biologically active metabolites.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, cycloalkyl, aryl, and alkylaryl esters such as methyl, ethyl, propyl, isopropyl, butyl, isobutyl, sec-butyl, tert-butyl, cyclopropyl, phenyl, benzyl, and phenethyl esters, and the like.

Compounds described herein may contain one or more asymmetrically substituted carbon and/or sulfur atoms, and may be isolated in optically active or racemic forms. Thus, all isomeric forms of a structure, including all stereogenic (such as enantiomeric, diastereomeric, and/or meso forms, whether chiral or racemic), all achiral, all geometric, and/or all conformational isomeric forms are intended, unless the specific stereochemical or other isomeric form is specifically indicated and/or achiral. It is well known in the art how to prepare and isolate such isomeric forms of a structure including those having stereogenic centers including those stereogenic forms wherein the structure is present in optically active form. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As used herein, the term "stereoisomers" refers to compounds that have identical chemical constitution, but differ as regards to the arrangement of the atoms or groups in space.

The terms "treatment" and "treating" as used herein include preventative (e.g., prophylactic), curative and/or palliative treatment. Also as used herein, the terms "treatment," "treating," and "treat" refer to reversing, alleviating, or inhibiting the progress of the disorder or condition to which the terms applies, or one or more symptoms of such disorder or condition.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker: New York, 1992, incorporated by reference herein in its entirety It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

It is further recognized that functional groups present on the compounds of Formula I and Formula IA may contain protecting groups. For example, the amino acid side chain substituents of the compounds of Formula I and Formula IA can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl ("Bn"), and methoxybenzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

For therapeutic purposes, the compounds of the present invention can be administered by any means that results in the contact of the active agent with the agent's site of action in the body of the subject. The compounds may be administered by any conventional means available for use in conjunction with pharmaceuticals, either as individual therapeutic agents or in combination with other therapeutic agents, such as, for example, analgesics. The compounds employed in the methods of the present invention including, for example, the compounds of Formula I and Formula IA may be administered by any means that results in the contact of the active agents with the agents' site or site(s) of action in the body of a patient. The compounds of the present invention are preferably administered in therapeutically effective amounts for the treatment of the diseases and disorders described herein to a subject in need thereof.

A therapeutically effective amount can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A preferred daily dose for adult humans includes about 25, 50, 100 and 200 mg, and an equivalent dose in a human child. The compounds may be administered in one or more unit dose forms. The unit dose ranges from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 µg/ml in a subject, and preferably about 1 to 20 µg/ml.

Although the compounds of the present invention may be administered as the pure chemicals, it is preferable to present the active ingredient as a pharmaceutical composition.

Generally speaking, therapeutic compounds of this invention may be administered to a patient alone or in combination with a pharmaceutically acceptable carrier. Accordingly, the compounds of the invention, for example, compounds of Formula I and Formula IA, are preferably combined with a pharmaceutical carrier selected on the basis of the chosen route of administration and standard pharmaceutical practice as described, for example, in *Remington's Pharmaceutical Sciences* (Mack Publishing Co., Easton, Pa., 1980), the disclosures of which are hereby incorporated herein by reference, in their entireties. The carrier(s) must be acceptable in the sense of being compatible with the other ingredients of the composition and not deleterious to the recipient thereof The relative proportions of active ingredient and carrier may be determined, for example, by the solubility and chemical nature of the compounds, chosen route of administration and standard pharmaceutical practice.

The compounds of the present invention may be formulated into pharmaceutical compositions by admixture with one or more pharmaceutically acceptable excipients. The excipients are selected on the basis of the chosen route of administration and standard pharmaceutical practice, as described, for example, in *Remington: The Science and Practice of Pharmacy*, $20^{th}$ ed.; Gennaro, A. R., Ed.; Lippincott Williams & Wilkins: Philadelphia, Pa., 2000. The compositions may be formulated to control and/or delay the release of the active agent(s), as in fast-dissolve, modified-release, or sustained-release formulations. Such controlled-release, or extended-release compositions may utilize, for example biocompatible, biodegradable lactide polymers, lactide/glycolide copolymers, polyoxyethylene-polyoxypropylene copolymers, or other solid or semisolid polymeric matrices known in the art.

The compositions can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders and the like.

For oral administration, the tablets, pills, powders, capsules, troches and the like can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; or flavoring agents such as peppermint or cherry flavoring. Capsules may contain any of the afore listed excipients, and may additionally contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers, and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

Pharmaceutical kits useful in, for example, the treatment of pain, which comprise a therapeutically effective amount of a compound of the invention and/or other therapeutic compounds described herein, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The compound of the invention and/or other therapeutic compound as described herein may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The compounds of the present invention may be used in methods to bind histamine receptors, more preferably histamine $H_3$ receptors. Such binding may be accomplished by contacting the receptor with an effective amount of a compound of Formula I or Formula IA. The histamine receptors may be located in the central nervous system or located peripherally to the central nervous system or in both locations. Preferably, the contacting step conducted in an aqueous medium, preferably at physiologically relevant ionic strength, pH, and the like.

In yet another aspect, the invention is directed to methods of binding histamine receptors, more preferably histamine $H_3$ receptors, comprising the step of administering to a patient in need thereof, an effective amount of a compound of the invention including, for example, a compound of Formula I or Formula IA.

In certain preferred aspects, the methods comprise the step of administering to said patient an therapeutically effective amount of a compound of Formula.

In some preferred embodiments, the histamine receptors are $H^3$ histamine receptors. In certain more preferred embodiments, the compound selectively binds $H^3$ histamine receptors relative to $H_1$, $H_2$ and/or $H_4$ receptors. In certain preferred embodiments, the $H^3$ histamine receptors are located in the central nervous system. In some other preferred embodiments, the compound of Formula I or Formula IA exhibits activity toward the histamine receptors. In certain preferred embodiments, the binding agonizes the activity of the cannabinoid receptors. In other preferred embodiments, the binding antagonizes the activity of the cannabinoid receptors, more preferably as a neutral antagonist. In still other preferred embodiments, the binding inversely agonizes the activity of the cannabinoid receptors.

In yet other preferred embodiments, the compounds of Formula I and Formula IA thereof exhibit activity toward the histamine receptors in vivo. In alternatively preferred embodiments, the compounds of Formula I and Formula IA exhibit activity toward the histamine receptors in vitro.

In certain other preferred aspects of the invention, there are provided methods of treating a disease, disorder or condition that may be affected, modulated or controlled through the binding of histamine, preferably $H_3$ histamine receptors. More preferably these diseases, disorders, and/or conditions selected from the group consisting of narcolepsy or sleep/wake disorders, feeding behavior disorders, eating disorders, obesity, cognition disorder, arousal disorder, memory disorder, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders, inflammation, and myocardial infarction. In preferred embodiments, the disease or disorder is narcolepsy or sleep/wake disorder. In other preferred embodiments, the disease or disorder is is attention deficit hyperactivity disorder. In still other embodiments, the disease or disorder is a cognition disorder. The methods herein provided comprise administering to a subject in need of such treatment a therapeutically effective amount of a compound of the invention, preferably a compound of Formula I or Formula IA.

In certain preferred embodiments, the disorder is narcolepsy or sleep/wake disorders. Alternatively the disorder treated is attention deficit hyperactivity disorder.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

Methods of Preparations

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

The general routes to prepare the examples shown herein are shown in the Schemes 1 to 6. The reagents and starting materials are commercially available, or readily synthesized by well-known techniques by one of ordinary skill in the arts. All substituents in the synthetic Schemes, unless otherwise indicated, are as previously defined.

Scheme 1: General Synthesis of Compounds of Formula I and Formula IA by Transition-Metal Catalyzed Coupling Reactions

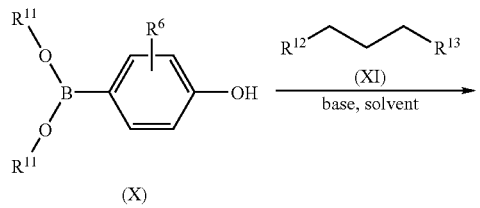

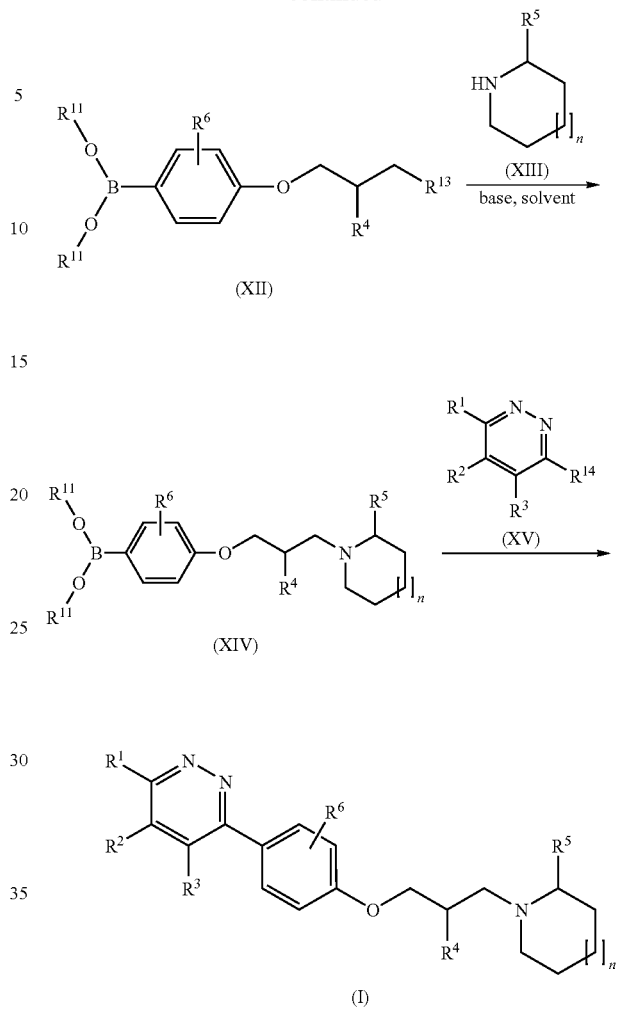

A boron ether derivative of general formula X, wherein $R^6$ is defined above and $R^{11}$ is for example lower alkyl, is alkylated with a substituted alkane of general formula XI, wherein $R^{12}$ and $R^{13}$ are suitable leaving groups such as bromine or chlorine, in the presence of a base, such as an alkali metal carbonate or a nitrogenous base such as triethylamine, in a suitable solvent such as toluene, a dialkyl ether, p-dioxane or tetrahydrofuran. The resultant ether derivative of general formula XII is then reacted in a nucleophilic displacement reaction, with an amine of general formula XIII, in the presence of a base and a suitable solvent, to provide a boron ether or boronic acid derivative of general formula XIV. This compound is subjected to a transition-metal catalyzed coupling reaction with a pyridazine derivative of general formula XV, wherein $R^1$, $R^2$ and $R^3$ are as defined above, and $R^{14}$ is a suitable leaving group, under conditions such as those corresponding to a Suzuki coupling reaction, in the presence of a suitable palladium catalyst as for example described in Cross-Coupling Reactions. A Practical Guide. [In: Top. Curr. Chem., 2002; 219] Miyaura, Norio; Editor. (2002), Publisher: (Springer-Verlag, Berlin, Germany), to provide a compound of general Formula I or Formula IA, wherein n and substituents $R^1$ to $R^6$ are as defined above. An example of detailed methodology for such reactions is illustrated in the procedure to provide Example 1.

Scheme 2: General Synthesis of Compounds of Formula I and Formula IA by an Alternate Transition-Metal Catalyzed Coupling Strategy

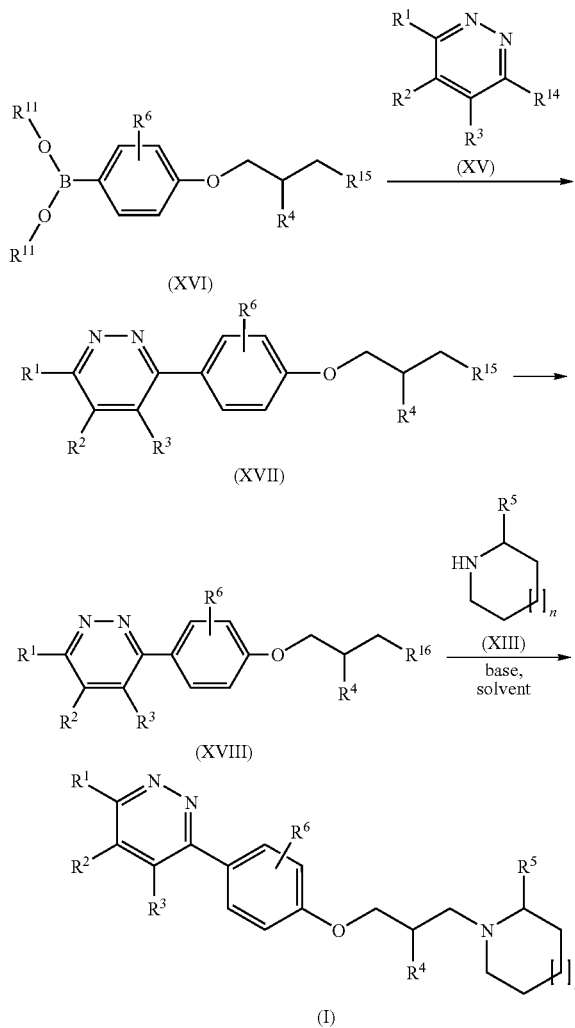

A boron ether or boronic acid derivative of general formula XVI, wherein $R^4$ and $R^6$ are as defined above, $R^{11}$ is for example lower alkyl or hydrogen, $R^{15}$ is for example an alcohol, or another functionality that can readily be converted into a leaving group by standard methods, is subjected to a transition-metal catalyzed coupling reaction, with a pyridazine derivative of general formula XV, wherein $R^1$, $R^2$ and $R^3$ are as defined above, and $R^{14}$ is a suitable leaving group, under conditions such as those corresponding to a Suzuki coupling reaction, in the presence of a suitable palladium catalyst as for example described in Cross-Coupling Reactions. A Practical Guide. [In: Top. Curr. Chem., 2002; 219] Miyaura, Norio; Editor. (2002), Publisher: (Springer-Verlag, Berlin, Germany), to provide a compound of general formula XVII. This product is converted into a compound of general formula XVIII, wherein $R^{16}$ is a suitable leaving group, for example a mesylate, a p-toluenesulfonate or a halogen such as bromine or chlorine. This intermediate XVIII is converted into a compound of general Formula I or IA, wherein n and substituents $R^1$ to $R^6$ are as described above, in a nucleophilic displacement reaction, with a cyclic amine of general formula XIII, in the presence of a base and a suitable solvent.

An example of detailed methodology for such reactions is illustrated in the procedure to provide Example 43.

Scheme 3: General Synthesis of Compounds of Formula I and Formula IA by a Reversed Transistion-metal Catalyzed Coupling Strategy

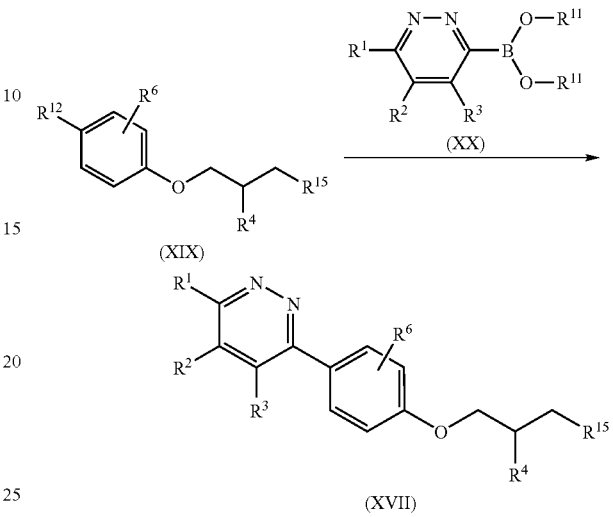

Scheme 4: General Synthesis of Compounds of Formula I and Formula IA by a Reversed Transistion-metal Catalyzed Coupling Strategy

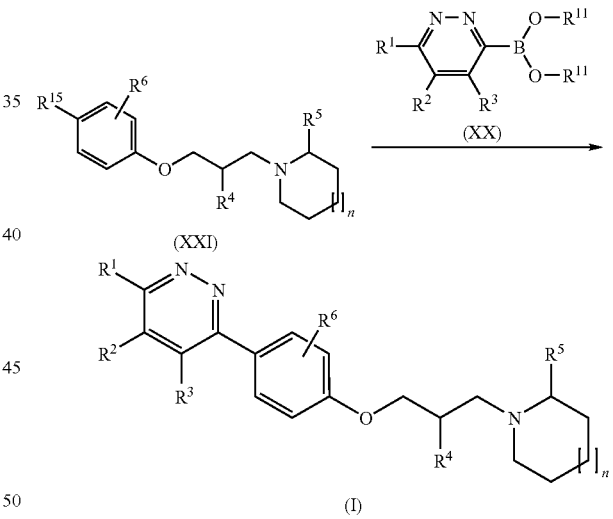

The transition-metal catalyzed coupling strategies for the synthesis of compounds of general formula XII or XVII illustrated in Schemes 1 and 2 are characterized for example by a phenyl boronic ester or related functionality reacting for example with a halogenated pyridazine derivative in the presence of a suitable palladium-derived catalyst. Usable alternatives exist whereby a compound of formula XIX, wherein $R^4$, $R^6$, $R^{12}$ and $R^{15}$ are as defined above, is allowed to react with a pyridazine-containing boron derivative, of formula XX, wherein $R^1$, $R^2$, $R^3$ and $R^{11}$ are defined above, using general methods as for example described in Cross-Coupling Reactions. A Practical Guide. [In: Top. Curr. Chem., 2002; 219] Miyaura, Norio; Editor. (2002), Publisher: (Springer-Verlag, Berlin, Germany), to provide a compound of general formula XVII, wherein substituents $R^1$ to $R^4$, $R^6$ and $R^{15}$ are as described above. This compound of formula XVII may be converted into a compound of formula I or IA by the procedures outlined in Scheme 2.

This strategy of a reversed transition-metal catalyzed coupling strategy is further illustrated by the reaction of a phenyl ether of general formula XXI, wherein n, $R^4$, $R^5$ $R^6$ are defined above, and $R^{15}$ is a suitable leaving group, is allowed to react with a pyridazine-containing boron derivative, of formula XX, wherein $R^1$, $R^2$, $R^3$ and $R^{11}$ are defined above, using general methods as for example described in Cross-Coupling Reactions. A Practical Guide. [In: Top. Curr. Chem., 2002; 219] Miyaura, Norio; Editor. (2002), Publisher: (Springer-Verlag, Berlin, Germany), to provide a compound of general Formula I or IA, wherein n and substituents $R^1$ to $R^6$ are as described above.

Scheme 5: Direct Displacement with a Nucleophile in Pyridazine 4-position

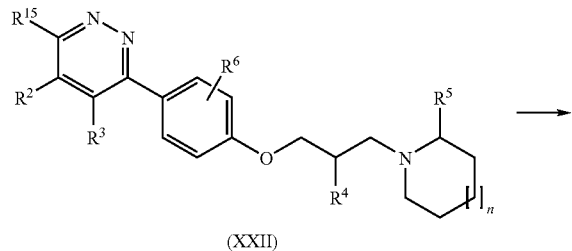

(XXII)

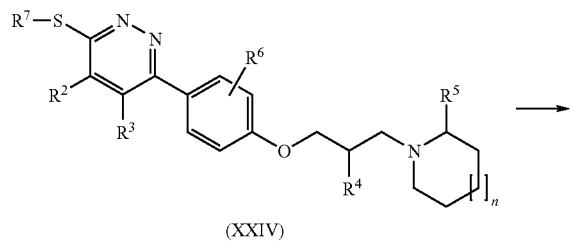

(I)

In cases where a preformed pyridazine derivative such as XXII is available by the general methods described herein, wherein n, substituents $R^2$ to $R^6$ are as defined above, and $R^{15}$ is a suitable leaving group, a compound of Formula I or IA may be generated by nucleophilic displacement by a range of nucleophiles, such as suitably substituted alcohols, thiols and amines, represented by the formulae $HOR^7$, $HSR^7$, $HNR^9R^{10}$ in the presence of an appropriate base.

An example of detailed methodology for such reactions is illustrated in the procedure to provide Example 20.

Scheme 6: Oxidation Procedure for Pyridazine 4-position

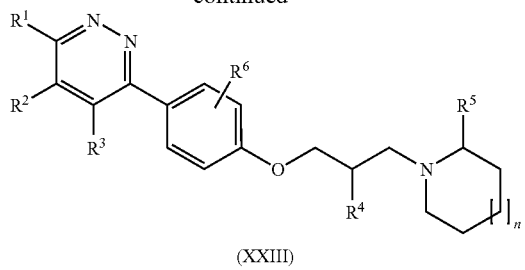

(XXIV)

(XXIII)

In examples where the $R^1$ group in an example such as compound XXIII is —$SOR^7$ or —$SO_2R^7$, wherein $R^7$, n and substituents $R^1$ to $R^6$ are as defined above, an oxidation reaction of a compound such as XXIV, wherein $R^7$ is as defined above may be carried out by a range of oxidizing agents, such as m-chloroperbenzoic acid, hydrogen peroxide or oxone. If the desired R1 group is —$SOR^7$, milder conditions may be used, such as Oxone in aqueous alcohol or tetrahydrofuran, at lowered temperature.

An example of detailed methodology for such reactions is illustrated in the procedure to provide Example 35.

Scheme 7: Pyridazine synthesis via the use of intermediate 1,4-diketone derivatives

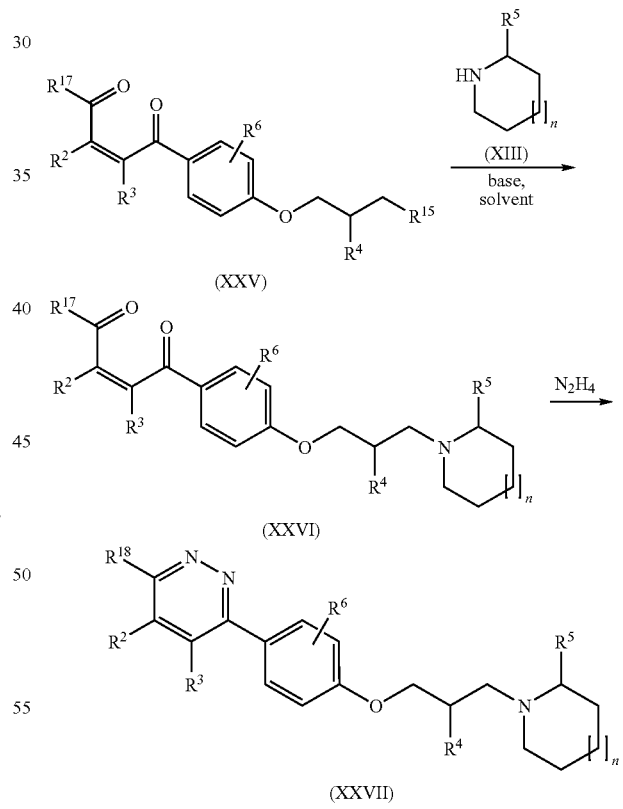

A 1,4-diketone derivative of general formula XXV, wherein $R^2$, $R^3$, $R^4$ and $R^6$ are as defined above, $R^{15}$ is a suitable leaving group, and $R^{17}$ is for example a hydroxyl group, is reacted with a cyclic amine of general formula XIII, wherein n and $R^5$ are as defined above, in the presence of a base and a suitable solvent, to provide a compound of general formula XXVI, wherein n, $R^2$, $R^3$, $R^4$, $R^5$, $R^6$ and $R^{17}$ are as defined above. The 1,4-diketone derivative XXVI is then reacted for example with hydrazine hydrate to provide a pyridazine derivative of formula XXVII, wherein n, $R^2$, $R^3$, $R^4$, $R^5$, $R^6$ are as defined above. In some cases $R^{18}$, which may initially be a hydroxyl group, will require further elaboration, for example by chlorination, utilizing reagents such as thionyl chloride or phosphorus oxychloride, to provide examples wherein $R^{18}$ is for example halogen. The product then represents a compound of Formula I or IA, or can readily be elaborated into further compounds of formula I or IA by methods described herein.

A range of further methods for conversion of 3-substituted phenoxypropylpyrrolidine derivatives and 3-substituted phenoxypropylpiperidine derivatives into the corresponding pyridazine derivatives are available, for example as described in standard textbooks of heterocyclic chemistry such as Heterocyclic Chemistry, Fourth Edition. Joule, J. A.; Mills, K. (2000). Publisher: Blackwell Science Ltd., Oxford, UK.

EXAMPLES

Example 1

—3-Chloro-6-{4-[3-((R)-2-methyl-pyrrolidin-1-yl)propoxy]-phenyl}pyridazine

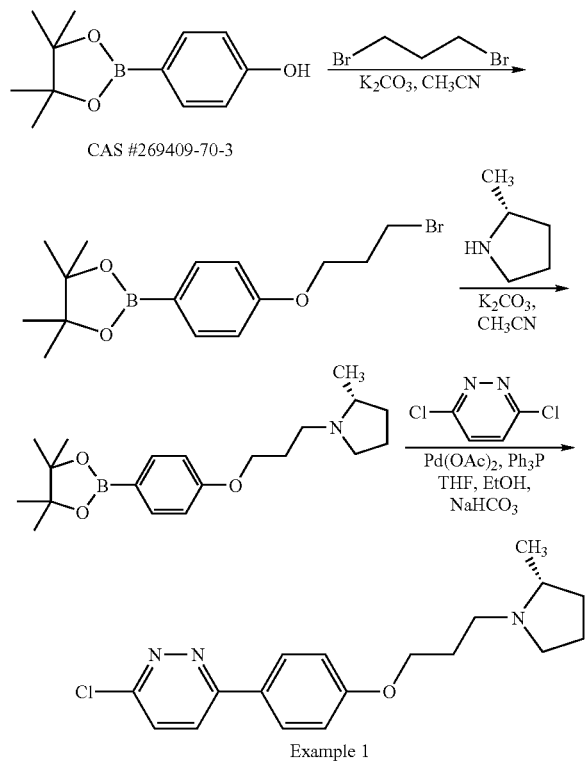

2-[4-(3-Bromopropoxy)phenyl]-4,4,5,5-tetramethyl-[1,3,2]-dioxaborolane 4-(4,4,5,5-Tetramethyl-[1,3,2]dioxaborolan-2-yl)-phenol (CAS #269409-70-3) (10.5 g, 47 mmol) was dissolved in dry $CH_3CN$ (200 mL) and dry, pulverized $K_2CO_3$ (10.4 g, 75 mmol) was introduced. 1,3-dibromopropane (38.1 mL, 375 mmol) was added dropwise, and the reaction mixture was heated at 70° C. for 7 h under a nitrogen atmosphere. The cooled reaction mixture was filtered and the filtrate was evaporated to an oily residue, which was applied to a column of silica gel. Elution initially with hexanes, gradually increasing polarity to a mixture of hexanes/ethyl acetate (25:1, 20:1 and 10:1) as eluent, provided the title compound (13.93 g, 86%) which crystallized on standing to a white solid, m.p. 62-65° C.

(R)-2-Methyl-1-{3-[4-(4,4,5,5-tetramethyl-[1,3,2]dioxaborolan-2-yl)-phenoxy]-propyl}-pyrrolidine 2-[4-(3-Bromopropoxy)phenyl]-4,4,5,5-tetramethyl-[1,3,2]-dioxaborolane (20.47 g, 60 mmol), (R)-2-methylpyrrolidine hydrochloride (7.663 g, 63 mmol) and dry, pulverized $K_2CO_3$ (24.96 g, 180 mmol) were mixed in dry $CH_3CN$ (650 mL). After stirring for 12 h at 78° C. under a nitrogen atmosphere, the reaction mixture was cooled and further (R)-2-methylpyrrolidine hydrochloride (10.0 g, 82 mmol) was introduced and heating at 78° C. was continued for 24 h. The reaction mixture was cooled, filtered and the filtrate was evaporated. Chromatography on silica gel, eluting initially with $CH_2Cl_2$, then with a mixture of $CH_2Cl_2$/EtOH/aq. $NH_3$ (290:10:1) and later with a (90:10:1) and (40:10:1) mixture of these solvents provided the title compound (17.44 g, 84%). The material crystallized on seeding. A sample was converted into a hydrochloride salt, m.p. 212-214° C.

3-Chloro-6-{4-[3(R)-2-methyl-pyrrolidin-1-yl)propoxy]phenyl}pyridazine (Example 1)

$Pd(OAc)_2$ trimer (2.02 g, 9.0 mmol) and $Ph_3P$ (9.36 g, 35.6 mmol) were suspended in anhydrous THF (300 mL) and stirred vigorously under a nitrogen atmosphere for 10 min. 3,6-dichloropyridazine (26.82 g, 180 mmol) was added as a solid and stirring was continued for 10 min. (R)-2-Methyl-1-{3-[4-(4,4,5,5-tetramethyl-[1,3,2]dioxaborolan-2-yl)-phenoxy]-propyl}-pyrrolidine (11.76 g, 34 mmol) was dissolved in a mixture of THF (200 mL) and EtOH (100 mL) and added dropwise to the reaction mixture. Saturated $NaHCO_3$ solution (360 mL) was introduced. The reaction mixture was heated at 80° C. for 15 h, cooled and was evaporated to a residue, which was taken up in $CH_2Cl_2$ (300 mL) and washed with water and saturated $NaHCO_3$ solution. The $CH_2Cl_2$ phase was dried ($Na_2SO_4$) and evaporated. The product was obtained by ISCO chromatography on silica gel, eluting with EtOAc initially, then with a mixture of EtOAc/$CH_3OH$ (9:1) to provide the title compound (10.20 g, 90%) as a cream solid, m.p. 107-108.5° C.; $^1H$ NMR ($CDCl_3$) 1.10 (d, 3H, —$CH_3$), 2.99 (m, 2H, —$CH_2$—), 3.18 (m, 2H, —$CH_2$—), 4.10 (m, 2H, —$CH_2$—), 7.04 (d, 2H, Ar—H), 7.50 (d, 1H, C—H), 7.78 (d, 1H, C—H), 7.99 (d, 2H, Ar—H) (representative signals only); HPLC retention time 6.893 min. (elution solvents $CH_3CN$ w/0.1% TFA and $H_2O$ w/0.1% TFA; column: Agilent Zorbax RX-C8 4.6 mm×150 mm w/5 μm particle size; method: 10-100% $CH_3CN$ over 20 min., 100% $CH_3CN$ for an additional 4.5 minutes; flow rate: 1.6 mL/min; System: Agilent 1100 HPLC).

The following examples were prepared by the procedure described in Example 1, a transition-metal catalyzed coupling reaction of the appropriate 3-halo pyridazine with (R)-2-methyl-1-{3-[4-(4,4,5,5-tetramethyl-[1,3,2]dioxaborolan-2-yl)phenoxy]propyl}pyrrolidine or 1-{3-[4-(4,4,5,5-tetramethyl-[1,3,2]dioxaborolan-2-yl)-phenoxy]propyl}piperidine:

TABLE I

| Example number | Structure | Melting Point (° C.) | HPLC Retention Time (min.) | NMR data |
|---|---|---|---|---|
| 2 | 3-Chloro-6-[4-(3-piperidin-1-yl-propoxy)-phenyl]-pyridazine | 140 | 2.035[a] | $^1$H NMR (CDCl$_3$) 2.45 (m, 2H, —CH$_2$—), 2.5 (m, 2H, —CH$_2$—), 4.10 (m, 2H, —CH$_2$—), 7.04 (d, 2H, Ar—H), 7.50 (d, 1H, C—H), 7.75 (d, 1H, C—H), 8.00 (d, 2H, Ar—H) |
| 3 | 3-Methyl-6-{4-[3-((R)-2-methyl-pyrrolidin-1-yl)-propoxy]-phenyl}pyridazine HCl salt | n/a | 4.188 | $^1$H NMR (CDCl$_3$) 1.12 (d, 3H, —CH$_2$—), 3.01 (m, 2H, —CH$_2$—), 3.20 (m, 2H, —CH$_2$—), 4.10 (m, 2H, —CH$_2$—), 7.02 (d, 2H, Ar—H), 7.34 (d, 1H, C—H), 7.69 (d, 1H, C—H), 8.02 (d, 2H, Ar—H) |
| 4 | 3-{4-[3-((R)-2-Methyl-pyrrolidin-1-yl)-propoxy]-phenyl}-6-phenyl-pyridazine | 158-160 | 7.926 | $^1$H NMR (CDCl$_3$) 1.12 (d, 3H, —CH$_3$), 3.03 (m, 2H, —CH$_2$—), 3.22 (m, 2H, —CH$_2$—), 4.13 (m, 2H, —CH$_2$—), 7.07 (d, 2H, Ar—H), 7.51 (d, 1H, C—H), 8.12 (d, 2H, Ar—H) |
| 5 | 3-{4-[3-((R)-2-Methyl-pyrrolidin-1-yl)-propoxy]-phenyl}-6-pyrrolidin-1-yl-pyridazine | 175-180 | 4.875 | $^1$H NMR (CDCl$_3$) 1.20 (d, 3H, CH$_3$), 3.09 (m, 2H, —CH$_2$—), 3.30 (m, 2H, —CH$_2$—), 4.10 (m, 2H, —CH$_2$—), 6.69 (d, 1H, C—H), 6.99 (d, 2H, Ar—H), 7.58 (d, 1H, C—H), 7.92 (d, 2H, Ar—H) |
| 6 | 4-(6-{4-[3-((R)-2-Methylpyrrolidin-1-yl)-propoxy]phenyl}pyridazin-3-yl)morpholine | n/a | 4.332 | $^1$H NMR (CDCl$_3$) 1.11 (d, 3H, —CH$_3$), 3.10 (m, 2H, —CH$_2$—), 3.19 (m, 2H, —CH$_2$—), 4.10 (m, 2H, —CH$_2$—), 6.96 (d, 1H, C—H), 7.00 (d, 2H, Ar—H), 7.63 (d, 1H, C—H), 7.94 (d, 2H, Ar—H) |

TABLE I-continued

| Example number | Structure | Melting Point (° C.) | HPLC Retention Time (min.) | NMR data |
|---|---|---|---|---|
| 7 | 6-{4-[3-((R)-2-Methyl-pyrrolidin-1-yl)-propoxy]-phenyl}-pyridazin-3-ylamine | 121-122 | 3.096 | $^1$H NMR (d$^6$-DMSO) 1.00 (d, 3H, —CH$_3$), 2.91 (m, 2H, —CH$_2$—), 3.08 (m, 2H, —CH$_2$—), 4.07 (m, 2H, —CH$_2$—), 6.81 (d, 1H, C—H), 7.01 (d, 2H, Ar—H), 7.73 (d, 1H, C—H), 7.89 (d, 2H, Ar—H) |
| 8 | Methyl-(6-{4-[3-((R)-2-methyl-pyrrolidin-1-yl)-propoxy]-phenyl}-pyridazin-3-yl)amine | 126-129 | 3.894 | $^1$H NMR (CDCl$_3$) 1.09 (d, 3H, —CH$_3$), 3.01 (m, 2H, —CH$_2$—), 3.20 (m, 2H, —CH$_2$—), 4.09 (m, 2H, —CH$_2$—), 6.69 (d, 1H, C—H), 6.97 (d, 2H, Ar—H), 7.58 (d, 1H, C—H), 7.91 (d, 2H, Ar—H) |
| 9 | 1-(6-{4-[3-((R)-2-Methylpyrrolidin-1-yl)-propoxy]phenyl}pyridazin-3-yl)piperidin-4-ol | 138-141 | 3.701 | $^1$H NMR (CDCl$_3$) 1.10 (d, 3H, —CH$_3$), 6.99 (d, 1H, C—H), 7.58 (d, 1H, C—H), 7.92 (d, 2H, Ar—H) |
| 10 | 3-Chloro-6-{3-methoxy-4-[3-((R)-2-methyl-pyrrolidin-1-yl)-propoxy}-phenyl}-pyridazine | 122 | 4.759$^b$ | $^1$H NMR (CDCl$_3$) 1.11 (d, 3H, —CH$_3$), 3.00 (m, 2H, —CH$_2$—), 3.20 (m, 2H, —CH$_2$—), 4.17 (m, 2H, —CH$_2$—), 7.03 (d, 1H, C—H), 7.50 (d, 1H, Ar—H), 7.60 (d, 1H, C—H), 7.82 (d, 2H, Ar—H) |
| 11 | 3-Chloro-6-[3-methoxy-4-(3-piperidin-1-yl-propoxy)-phenyl]-pyridazine | 120 | 4.780$^b$ | $^1$H NMR (CDCl$_3$) 2.40 (m, 2H, —CH$_2$—), 4.18 (m, 2H, —CH$_2$—), 7.01 (d, 1H, C—H), 7.48 (d, 1H, Ar—H), 7.52 (d, 1H, Ar—H), 7.80 (d, 1H, Ar—H) |

TABLE I-continued

| Example number | Structure | Melting Point (° C.) | HPLC Retention Time (min.) | NMR data |
|---|---|---|---|---|
| 12 | 3-Chloro-6-[2-methyl-4-(3-piperidin-1-yl-propoxy)-phenyl]-pyridazine | 85 | 5.007[b] | $^1$H NMR (CDCl$_3$) 2.01 (m, 2H, —CH$_2$—), 2.50 (m, 2H, —CH$_2$—), 4.10 (m, 2H, —CH$_2$—), 6.88 (d, 2H, C—H), 6.95 (d, 2H, Ar—H), 7.40 (d, 1H, C—H) 7.55 (s, 1H, Ar—H) |
| 13 | 5-(6-Chloro-pyridazin-3-yl)-2-[3-((R)-2-methyl-pyrrolidin-1-yl)-propoxy]benzonitrile | 134-136 | 2.742[c] | $^1$H NMR (d$^6$-DMSO) 1.00 (d, 3H, —CH$_3$), 4.29 (m, 2H, —CH$_2$—), 7.45 (d, 1H, C—H), 8.04 (d, 1H, C—H), 8.40 (d, 1H, C—H), 8.48-8.53 (m, 2H, Ar—H) |
| 14 | 5-(6-Chloro-pyridazin-3-yl)-2-(3-piperidin-1-yl-propoxy)benzonitrile | 140-142 | 2.844[c] | $^1$H NMR (CDCl$_3$) 2.35 (m, 4H, —CH$_2$—), 4.26 (m, 2H, —CH$_2$—), 7.20 (d, 1H, C—H), 7.60 (d, 1H, Ar—H), 7.81 (d, 1H, C—H) 8.34 (d, 1H, Ar—H) |
| 15 | 1-Chloro-4-[4-(3-piperidin-1-yl-propoxy)-phenyl]-6,7-dihydro-5H-cyclopenta[d]pyridazine | 120 | 2.368[a] | $^1$H NMR (CDCl$_3$) 3.06 (m, 2H, —CH$_2$—), 3.20 (m, 2H, —CH$_2$—), 4.10 (m, 2H, —CH$_2$—), 7.05 (d, 2H, Ar—H), 7.80 (d, 2H, Ar—H) |
| 16 | 3-{4-[3-((R)-2-Methyl-pyrrolidin-1-yl)propoxy]-phenyl}-6-thiophen-2-yl-pyridazine | 108 | 2.373[a] | $^1$H NMR (CDCl$_3$) 1.13 (d, 3H, —CH$_3$), 3.00 (m, 2H, —CH$_2$—), 3.19 (m, 2H, —CH$_2$—), 4.09 (m, 2H, —CH$_2$—), 6.72 (d, 1H, C—H), 7.00 (d, 2H, Ar—H), 7.70 (d, 1H, C—H), 8.10 (d, 2H, Ar—H) |

TABLE I-continued

| Example number | Structure | Melting Point (° C.) | HPLC Retention Time (min.) | NMR data |
|---|---|---|---|---|
| 17 | 3-{4-[3-((R)-2-Methyl-pyrrolidin-1-yl)propoxy]-phenyl}-6-thiophen-2-yl-pyridazine | 65 | 2.364[a] | $^1$H NMR (CDCl$_3$) 1.09 (d, 3H, —CH$_3$), 3.05 (m, 2H, —CH$_2$—), 3.20 (m, 2H, —CH$_2$—), 4.10 (m, 2H, —CH$_2$—), 7.05 (d, 2H, Ar—H), 7.80 (d, 2H, Ar—H) |
| 18 | 3-Chloro-6-{4-[3-((R)-2-methyl-pyrrolidin-1-yl)propoxy]-phenyl}-4,5-diaza-tricyclo[6.2.2.0*2,7*]-dodeca-2(7),3,5-triene | 132-134 | 9.345 | $^1$H NMR (CDCl$_3$) 1.10 (d, 3H, —CH$_3$), 3.00 (m, 2H, —CH$_2$—), 3.19 (m, 2H, —CH$_2$—), 4.10 (m, 2H, —CH$_2$—), 7.03 (d, 2H, Ar—H), 7.54 (d, 2H, Ar—H) |
| 19 | 3-(5-Chloro-pyridin-3-yloxy)-6-{4-[3-((R)-2-methyl-pyrrolidin-1-yl)-propoxy-phenyl}-pyridazine | 119 | 8.560 | $^1$H NMR (CDCl$_3$) 1.10 (d, 3H, —CH$_3$) 2.99 (m, 2H, —CH$_2$—), 3.20 (m, 2H, —CH$_2$—), 4.10 (m, 2H, —CH$_2$—), 7.01 (d, 1H, C—H), 7.30 (d, 2H, Ar—H), 7.95 (d, 2H, Ar—H), 8.50 (d, 1H, C—H) |

[a] HPLC conditions as described in Example 1, but with a gradient of 10-100% CH$_3$CN over 5 min
[b] HPLC conditions 10-100% CH$_3$CN over 10 min
[c] HPLC conditions 10-100% CH$_3$CN over 8 min Example 20

3-Benzyloxy-6-[4-(3-piperidin-1-yl-propoxy)phenyl]pyridazine

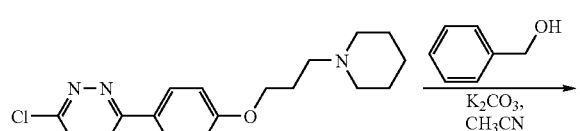

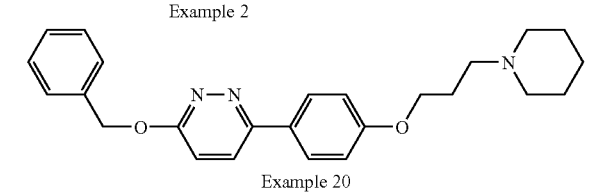

Sodium hydride (0.007 g, 0.18 mmol) was stirred in anhydrous DMF (4 mL) under a nitrogen atmosphere, and benzyl alcohol (0.016 g, 0.15 mmol) was added. After 15 min., 3-chloro-6-[4-(3-piperidin-1-yl-propoxy)-phenyl]-pyridazine (0.05 g, 0.15 mmol) was introduced, and the reaction mixture was stirred at room temperature for 5 h. The precipitate was collected by filtration, washed with H$_2$O (10 mL) and dried in vacuo to provide the title compound as a white solid (0.050 g, 83%), m.p. 138° C.; $^1$H NMR (CDCl$_3$) 2.00 (m, 2H, —CH$_2$—), 2.50 (m, 2H, —CH$_2$—), 4.10 (m, 2H, —CH$_2$—), 7.00 (d, 1H, C—H), 7.05 (d, 2H, Ar—H), 7.75 (d, 1H, C—H), 7.95 (d, 2H, Ar—H) HPLC retention time 2.612 min[a].

Example 35

3-{4-[3-((R)-2-Methylpyrrolidin-1-yl)propoxy]phenyl}-6-phenylmethanesulfinyl-pyridazine

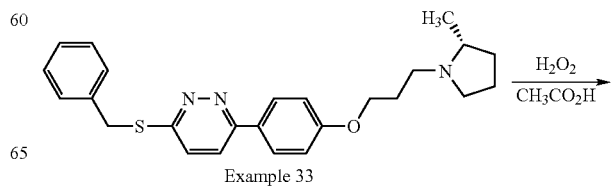

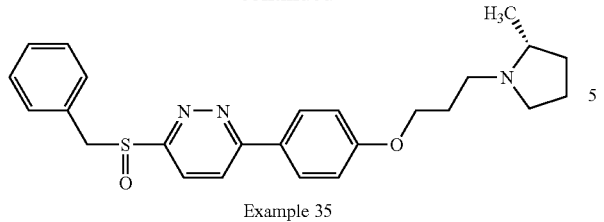

Example 35

3-Benzylsulfanyl-6-{4-[3-((R)-2-methyl-pyrrolidin-1-yl)-propoxy]-phenyl}-pyridazine (0.08 g, 0.19 mmol) was dissolved in CH$_3$CO$_2$H (3 mL) and a 50% solution of H$_2$O$_2$ in H$_2$O (0.026 mL, 0.16 mmol) was introduced. The reaction mixture was stirred and monitored by LC-MS, and after 5 h was evaporated to a residue, which was treated with H$_2$O (20 mL) and CH$_2$Cl$_2$ (30 mL). The organic layer was washed with saturated NaHCO$_3$ solution (20 mL), saturated brine (10 mL) and dried (MgSO$_4$) before being evaporated to a white solid (0.051 g, 64%), m.p. 145° C.

Example 37

3-{4-[3-((R)-2-Methyl-pyrrolidin-1-yl)-propoxy]phenyl}-6-phenylmethanesulfonyl-pyridazine

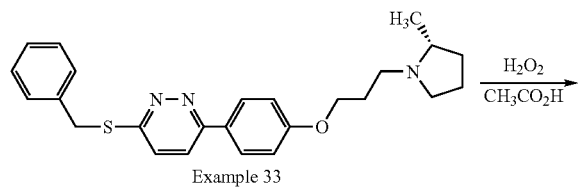

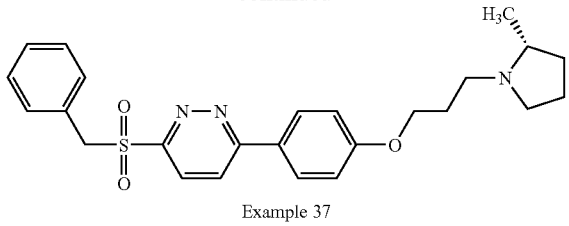

Example 37

3-Benzylsulfanyl-6-{4-[3-((R)-2-methyl-pyrrolidin-1-yl)-propoxy]-phenyl}-pyridazine (0.065 g, 0.15 mmol) was dissolved in CH$_3$CH$_2$OH (3 mL) and a solution of "Oxone", potassium peroxymonosulphate (0.36 g, 0.23 mmol) in H$_2$O (1 mL) was introduced. The reaction mixture was stirred and monitored by LC-MS, and after 2 h was evaporated to a residue, which was treated with EtOAc (20 mL) washed with saturated NaHCO$_3$ solution (20 mL), saturated brine (10 mL) and dried (MgSO$_4$) before being evaporated to a white solid (0.028 g, 40%), m.p. 136° C.

The following examples were prepared by the procedures described in Examples 20, 35 and 37. In some cases, such as in Examples 35-38, further sulfur oxidation stages are required to prepare the compounds described, as illustrated in Examples 35 and 37.

TABLE II

| Example number | Structure | Melting Point (° C.) | HPLC Retention Time (min.) | NMR data |
|---|---|---|---|---|
| 21 | 3-Benzyloxy-6-{4-[3-((R)-2-methyl-pyrrolidin-1-yl)-propoxy]-phenyl}-pyridazine | 114 | 2.575[a] | $^1$HNMR (CDCl$_3$) 1.11 (d, 3H, —CH$_3$), 3.00 (m, 2H, —CH$_2$—), 3.19 (m, 2H, —CH$_2$—), 4.10 (m, 2H, —CH$_2$—), 7.05 (d, 1H, C—H), 7.40 (d, 2H, Ar—H), 7.75 (d, 1H, C—H), 7.95 (d, 2H, Ar—H) |
| 22 | 3-Methoxy-6-{4-[3-((R)-2-methyl-pyrrolidin-1-yl-propoxy]-phenyl}pyridazine | 121 | 1.687[a] | $^1$H NMR (CDCl$_3$) 1.12 (d, 3H, —CH$_3$), 2.98 (m, 2H, —CH$_2$—), 3.20 (m, 2H, —CH$_2$—), 4.15 (m, 2H, —CH$_2$—), 7.00 (d, 2H, Ar—H), 7.31 (d, 1H, C—H), 7.75 (d, 1H, C—H), 7.95 (d, 2H, Ar—H) |

TABLE II-continued

| Example number | Structure | Melting Point (° C.) | HPLC Retention Time (min.) | NMR data |
|---|---|---|---|---|
| 23 | 3-Methoxy-6-{4-3-piperidin-1-yl-propoxy)-phenyl]pyridazine | 116 | 1.683[a] | $^1$H NMR (CDCl$_3$) 2.75 (m, 4H, —CH$_2$—), 4.10 (m, 2H, —CH$_2$—), 7.00 (d, 1H, C—H), 7.05 (d, 2H, Ar—H), 7.75 (d, 1H, C—H), 7.95 (d, 2H, Ar—H) |
| 24 | 3-Isopropoxy-6-{4-[3-((R)-2-methyl-pyrrolidin-1-yl)-propoxy]-phenyl}pyridazine | 75 | 2.134[a] | $^1$H NMR (CDCl$_3$) 1.60 (d, 3H, —CH$_3$), 2.20 (m, 2H, —CH$_2$—), 2.98 (m, 2H, —CH$_2$—), 4.11 (m, 2H, —CH$_2$—), 7.28 (d, 2H, Ar—H), 7.40 (d, 2H, Ar—H) |
| 25 | 3-Phenoxy-6-[4-(3-piperidin-1-yl-propoxy)-phenyl]pyridazine | 139 | 2.544[a] | $^1$H NMR (CDCl$_3$) 4.10 (m, 2H, —CH$_2$—), 6.98 (d, 2H, Ar—H), 7.25 (d, 1H, C—H), 7.83 (d, 1H, C—H), 7.97 (d, 2H, Ar—H) |
| 26 | 3-(4-Fluoro-benzyloxy)-6-{4-[3-((R)-2methyl-pyrrolidin-1-yl)propoxy]-phenyl}pyridazine | 118 | 2.658[a] | $^1$H NMR (CDCl$_3$) 1.10 (d, 3H, —CH$_3$), 3.00 (m, 2H, —CH$_2$—), 3.19 (m, 2H, —CH$_2$—), 4.10 (m, 2H, —CH$_2$—), 7.00 (d, 1H, C—H), 7.03 (d, 2H, Ar—H), 7.75 (d, 1H, C—H), 7.95 (d, 2H, Ar—H) |
| 27 | 3-{4-[3-((R)-2-Methyl-pyrrolidin-1-yl)-propoxy]-phenyl}-6-(4-trifluoro-methyl-benzyloxy)pyridazine | 160 | 3.018[a] | $^1$H NMR (CDCl$_3$) 1.10 (d, 3H, —CH$_3$), 2.98 (m, 2H, —CH$_2$—), 3.18 (m, 2H, —CH$_2$—), 4.10 (m, 2H, —CH$_2$—), 7.00 (d, 1H, C—H), 7.10 (d, 2H, Ar—H), 7.85 (d, 1H, C—H), 7.95 (d, 2H, Ar—H) |

TABLE II-continued

| Example number | Structure | Melting Point (° C.) | HPLC Retention Time (min.) | NMR data |
|---|---|---|---|---|
| 28 | Ethyl-(6-{4-[3-((R)-2-methyl-pyrrolidin-1-yl)-propoxy]-phenyl}-pyridazin-3-yl)amine | n/a | 4.509 | $^1$H NMR (CDCl$_3$) 1.37 (d, 3H, —CH$_3$), 3.13 (m, 2H, —CH$_2$—), 3.38 (m, 2H, —CH$_2$—), 4.09 (m, 2H, —CH$_2$—), 6.89 (d, 1H, C—H), 6.96 (d, 2H, Ar—H), 7.62 (d, 1H, C—H), 7.77 (d, 2H, Ar—H) |
| 29 | Benzyl-(6-{4-[3-((R)-2-methyl-pyrrolidin-1-yl)-propoxy]-phenyl}-pyridazin-3-yl)-amine | 139.5–141 | 6.904 | $^1$H NMR (CDCl$_3$) 1.13 (d, 3H, —CH$_3$), 3.01 (m, 2H, —CH$_2$—), 3.21 (m, 2H, —CH$_2$—), 4.09 (m, 2H, —CH$_2$—), 6.69 (d, 1H, C—H), 6.97 (d, 2H, Ar—H), 7.56 (d, 1H, C—H), 7.89 (d, 2H, Ar—H) |
| 30 | 3-{4-[3-((R)-2-Methyl-pyrrolidin-1-yl-propoxy]-phenyl}-6-methylsulfanyl-pyridazine | 101 | 2.253$^a$ | $^1$H NMR (CDCl$_3$) 1.11 (d, 3H, —CH$_3$), 2.98 (m, 2H, —CH$_2$—), 3.19 (m, 2H, —CH$_2$—), 4.10 (m, 2H, —CH$_2$—), 7.00 (d, 2H, Ar—H), 7.60 (d, 1H, C—H), 8.00 (d, 2H, Ar—H) |
| 31 | 3-Methylsulfanyl-6-[4-(3-piperidin-1-yl-propoxy)-phenyl]-pyridazine | 122 | 1.975$^a$ | $^1$H NMR (CDCl$_3$) 2.40 (m, 2H, —CH$_2$—), 2.61 (m, 2H, —CH$_2$—), 4.05 (m, 2H, —CH$_2$—), 7.10 (d, 2H, Ar—H), 7.4 (d, 1H, C—H), 7.60 (d, 1H, C—H), 8.00 (d, 2H, Ar—H) |
| 32 | 1-{4-[3-((R)-2-Methyl-pyrrolidin-1-yl)propoxy]-phenyl}-4-methylsulfanyl-6,7-dihydro-5H-cyclopenta[d]pyridazine | n/a | 1.966$^a$ | $^1$H NMR (CDCl$_3$) 1.11 (d, 3H, —CH$_3$), 2.89 (m, 2H, —CH$_2$—), 3.17 (m, 2H, —CH$_2$—), 4.10 (m, 2H, —CH$_2$—), 7.00 (d, 2H, Ar—H), 7.80 (d, 2H, Ar—H) |

TABLE II-continued

| Example number | Structure | Melting Point (° C.) | HPLC Retention Time (min.) | NMR data |
|---|---|---|---|---|
| 33 | 3-Benzylsulfanyl-6-{4-[3-((R)-2-methyl-pyrrolidin-1-yl)-propoxy]-phenyl}-pyridazine | 104 | 2.789[a] | $^1$H NMR (CDCl$_3$) 1.10 (d, 3H, —CH$_3$), 3.00 (m, 2H, —CH$_2$—), 3.21 (m, 2H, —CH$_2$—), 4.11 (m, 2H, —CH$_2$—), 6.75 (d, 1H, C—H), 7.01 (d, 2H, Ar—H), 7.65 (d, 1H, C—H), 8.00 (d, 2H, Ar—H) |
| 34 | 3-Benzylsulfanyl-6-[4-(3-piperidin-1-yl-propoxy)-phenyl]-pyridazine | 144 | 2.822 | $^1$H NMR (CDCl$_3$) 2.05 (m, 2H, —CH$_2$—), 2.52 (m, 2H, —CH$_2$—), 4.05 (m, 2H, —CH$_2$—), 7.00 (d, 1H, C—H), 7.30 (d, 2H, Ar—H), 7.60 (d, 1H, C—H), 8.00 (d, 2H, Ar—H) |
| 35 | 3-{4-[3-((R)-2-Methyl-pyrrolidin-1-yl)propoxy]-phenyl}-6-phenylmethanesulfinyl-pyridazine | 145 | 2.238[a] | $^1$H NMR (CDCl$_3$) 1.12 (d, 3H, —CH$_3$), 3.00 (m, 2H, —CH$_2$—), 3.22 (m, 2H, —CH$_2$—), 4.12 (m, 2H, —CH$_2$—), 7.65 (d, 1H, C—H), 7.83 (d, 1H, C—H), 8.09 (d, 2H, Ar—H) |
| 36 | 3-Phenylmethanesulfinyl-6-[4-(3-piperidin-1-yl-propoxy)-phenyl]-pyridazine | 186 | 2.238[a] | $^1$H NMR (CDCl$_3$) 2.41 (m, 2H, —CH$_2$—), 2.50 (m, 2H, —CH$_2$—), 4.10 (m, 2H, —CH$_2$—), 7.03 (d, 2H, Ar—H), 7.23 (d, 1H, C—H), 7.85 (d, 1H, C—H), 8.10 (d, 2H, Ar—H) |

TABLE II-continued

| Example number | Structure | Melting Point (° C.) | HPLC Retention Time (min.) | NMR data |
|---|---|---|---|---|
| 37 | 3-{4-[3-((R)-2-Methyl-pyrrolidin-1-yl)-propoxy]-phenyl}-6-phenylmethanesulfonyl-pyridazine | 136 | 2.619[a] | $^1$H NMR (CDCl$_3$) 1.10 (d, 3H, —CH$_3$), 3.05 (m, 2H, —CH$_2$—), 3.20 (m, 2H, —CH$_2$—), 4.10 (m, 2H, —CH$_2$—), 7.02 (d, 2H, Ar—H), 7.30 (d, 1H, C—H), 7.85 (d, 1H, C—H), 8.15 (d, 2H, Ar—H) |
| 38 | 3-Phenylmethanesulfonyl-6-[4-(3-piperidin-1-yl-propoxy)-phenyl]-pyridazine | 134 | 6.15[c] | $^1$H NMR (CDCl$_3$) 2.05 (m, 2H, —CH$_2$—), 2.525 (m, 2H, —CH$_2$—), 4.05 (m, 2H, —CH$_2$—), 7.00 (d, 1H, C—H), 7.03 (d, 2H, Ar—H), 7.85 (d, 1H, C—H), 8.10 (d, 2H, Ar—H) |
| 39 | 1-Methoxy-4-{4-[3-((R)-2-methylpyrrolidin-1-yl)-propoxy]-phenyl}6,7-dihydro-5H-cyclopenta[d]pyridazine | 109 | 1.712[a] | $^1$H NMR (d$^6$-DMSO) 1.40 (d, 3H, —CH$_3$), 2.90 (m, 2H, —CH$_2$—), 3.15 (m, 2H, —CH$_2$—), 4.15 (m, 2H, —CH$_2$—), 7.12 (d, 2H, Ar—H), 7.80 (d, 2H, Ar—H) |
| 40 | 1-Methoxy-4-{4-[3-((R)-2-methyl-pyrrolidin-1-yl-propoxy]-phenyl}phthalazine | 111 | 1.744[a] | $^1$H NMR (CDCl$_3$) 1.11 (d, 3H, —CH$_3$), 3.00 (m, 2H, —CH$_2$—), 3.20 (m, 2H, —CH$_2$—), 4.10 (m, 2H, —CH$_2$—), 7.10 (d, 2H, Ar—H), 7.72 (d, 2H, Ar—H) |
| 41 | 3-Benzofuran-2-yl-6-{4-[3-((R)-2-methyl-pyrrolidin-1-yl)-propoxy]-phenyl}-pyridazine | 180 | 9.784 CHPM | $^1$H NMR (CDCl$_3$) 1.09 (d, 3H, —CH$_3$), 3.00 (m, 2H, —CH$_2$—), 3.20 (m, 2H, —CH$_2$—), 4.10 (m, 2H, —CH$_2$—), 7.05 (d, 1H, C—H), 7.32 (d, 2H, Ar—H), 7.40 (d, 1H, C—H), 8.10 (d, 2H, Ar—H) |

TABLE II-continued

| Example number | Structure | Melting Point (°C.) | HPLC Retention Time (min.) | NMR data |
|---|---|---|---|---|
| 42 | 1-Benzylsulfanyl-4-{4-[3-((R)-2-methyl-pyrrolidin-1-yl)propoxy]-phenyl}-6,7-dihydro-5H-cyclopenta[d]pyridazine | 122 | 2.708$^a$ | $^1$H NMR (CDCl$_3$) 1.10 (d, 3H, —CH$_3$), 3.00 (m, 2H, —CH$_2$—), 3.19 (m, 2H, —CH$_2$—), 4.10 (m, 2H, —CH$_2$—), 7.00 (d, 2H, Ar—H), 7.80 (d, 2H, Ar—H) |

Example 43

3-Chloro-6-{4-[(S)-2-methyl-3-((R)-2-methylpyrrolidin-1-yl)propoxy]-phenyl}pyridazine

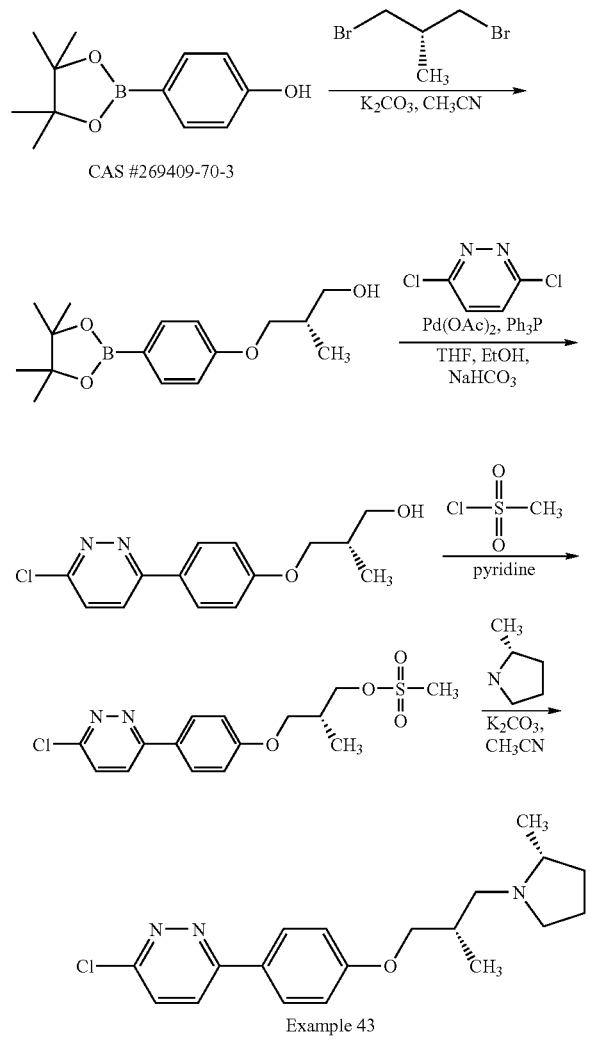

Example 43

(S)-2-Methyl-3-[4-(4,4,5,5-tetramethyl-[1,3,2]dioxaborolan-2-yl)-phenoxy]-propan-1-ol (S)-3-Bromo-2-methylpropan-1-ol (6.2 g, 40 mmol) was dissolved in dry CH$_3$CN (100 mL) and dry, pulverized K$_2$CO$_3$ (10.4 g, 75 mmol) was introduced followed by 4-(4,4,5,5-tetramethyl-[1,3,2]dioxaborolan-2-yl)-phenol (11.0 g, 50 mmol). The reaction mixture was heated at 72° C. for 20 h, cooled and filtered. The filtrate was evaporated to an oil, which was applied to a column of silica gel. Elution initially with hexanes, gradually increasing polarity to a mixture of hexanes/ethyl acetate (3:2) as eluent, provided the title compound (7.56 g, 64%) as an oil.

(S)-3-[4-(6-Chloro-pyridazin-3-yl)-phenoxy]-2-methyl-propan-1-ol

Pd(OAc)$_2$ trimer (0.84 g, 3.75 mmol) and Ph$_3$P (3.9 g, 15 mmol) were suspended in anhydrous THF (200 mL) and stirred vigorously under a nitrogen atmosphere for 10 min. 3,6-dichloropyridazine (8.94 g, 60 mmol) was added as a solid and stirring was continued for 45 min.

A solution of (S)-2-Methyl-3-[4-(4,4,5,5-tetramethyl-[1,3,2]dioxaborolan-2-yl)phenoxy]propan-1-ol (4.38 g, 15 mmol) in a mixture of THF (50 mL) and EtOH (20 mL) was added dropwise to the reaction mixture. Saturated NaHCO$_3$ solution (120 mL) was introduced. The reaction mixture was heated at 74° C. for 24 h, cooled, filtered and was evaporated to a residue, which was taken up in CH$_2$Cl$_2$ (300 mL) and washed with water and saturated NaHCO$_3$ solution. The CH$_2$Cl$_2$ phase was dried (Na$_2$SO$_4$) and evaporated. The title compound was obtained by ISCO chromatography on silica gel, eluting with hexanes/EtOAc (9:1) initially, gradually increasing polarity to a 1:2 mixture of these solvents, to provide the title compound (3.22 g, 78%) as a white solid, m.p. 134-138° C.; $^1$H NMR (CDCl$_3$) 1.10 (d, 3H, —CH$_3$), 2.22 (1H, m, C—H), 3.72 (m, 2H, —CH$_2$—), 4.04 (m, 2H, —CH$_2$—), 7.04 (d, 2H, Ar—H), 7.51 (d, 1H, C—H), 7.80 (d, 1H, C—H), 8.00 (d, 2H, Ar—H); HPLC retention time 8.843 min. (elution solvents CH$_3$CN w/0.1% TFA and H$_2$O w/0.1% TFA); 10-100% CH$_3$CN over 20 min.

3-Chloro-6-{4-[(S)-2-methyl-3-((R)-2-methylpyrrolidin-1-yl)propoxy]phenyl}-pyridazine (Example 43)

(S)-3-[4-(6-Chloro-pyridazin-3-yl)phenoxy]-2-methyl-propan-1-ol (3.0 g, 10.76 mmol) was dissolved in a mixture of pyridine (10 mL) and THF (90 mL), and the solution cooled to 0° C. Methanesulfonyl chloride (2.863 g, 25 mmol) was introduced dropwise, and the reaction mixture was stirred at ambient temperature for 20 h. EtOAc (100 mL) and $H_2O$ (150 mL) were added, separated, and the aqueous layer was extracted further with EtOAc (2×100 mL). The combined extracts were dried ($MgSO_4$) and evaporated to a solid which was purified by column chromatography on silica gel, eluting with a gradient of hexane/EtOAc to provide the intermediate methanesulfonic acid (R)-3-[4-(6-chloro-pyridazin-3-yl)-phenoxy]-2-methylpropyl ester (3.52 g, 91%). This intermediate (7 mmol) was treated with (R)-2-methylpyrrolidine, benzenesulfonic acid salt (3.65 g, 15 mmol) and dry, pulverized $K_2CO_3$ (4.15 g, 30 mmol) in dry $CH_3CN$ (200 mL). The reaction mixture was heated at reflux for 30 h and cooled, filtered and the filtrate evaporated. The residue was purified by column chromatography, eluting with a gradient mixture of $CH_2Cl_{12}$ and EtOH containing 10% of aqueous ammonia solution, to provide the title compound (1.46 g, 60%), m.p. 152-155° C., $^1$H NMR ($CDCl_3$) 1.18 (d, 3H, —$CH_3$), 1.27 (d, 3H, —$CH_3$), 3.98 (m, 2H, —$CH_2$—), 7.02 (d, 2H, Ar—H), 7.52 (d, 1H, C—H), 7.78 (d, 1H, C—H), 8.02 (d, 2H, Ar—H); HPLC retention time 7.530 min. (elution solvents $CH_3CN$ w/0.1% TFA and $H_2O$ w/0.1% TFA); 10-100% $CH_3CN$ over 20 min.

The following example was prepared by the procedure described in Example 43.

$K_2CO_3$ (1.19 g, 8.6 mmol) in 1,2-dimethoxyethane (25 mL) and water (11.5 mL) were combined and degassed with argon. The reaction was heated at 85° C. for 15 h, cooled to rt, filtered through celite, taken up in $CH_2Cl_2$ (30 mL) and washed with water and saturated $NaHCO_3$ solution. The $CH_2Cl_2$ layer was dried ($Na_2SO_4$) and evaporated. The product was purified by ISCO chromatography on silica gel, eluting with 5-15% MeOH/DCM/0.5% $NH_4OH$. The HCl salt was prepared MeOH-ether-HCl to give a white solid, m.p. 198-201° C.; LCMS m/z=298 (M+1).

The compounds of the present invention are useful, inter alia, as therapeutic agents. Particularly, the compounds are useful for interacting with the $H_3$ receptor. In one embodiment, the present invention provides a method for treating or preventing diseases and disorders, such as those disclosed herein, which comprises administering to a subject in need of such treatment or prevention a therapeutically effective amount of a compound of the present invention.

In an additional embodiment, the present invention provides a method for inhibiting $H_3$ activity comprising providing a compound of the present invention in an amount sufficient to result in effective inhibition. Particularly, the compounds of the present invention can be administered to treat such diseases and disorders such as narcolepsy or other sleep/wake disorders, such as obstructive sleep apnea/hypopnea syndrome, and shift work sleep disorder; feeding behavior, eating disorders, obesity, cognition, arousal, memory,

TABLE III

| Example number | Structure | Melting Point (° C.) | HPLC Retention Time (min.) | NMR data |
|---|---|---|---|---|
| 44 | 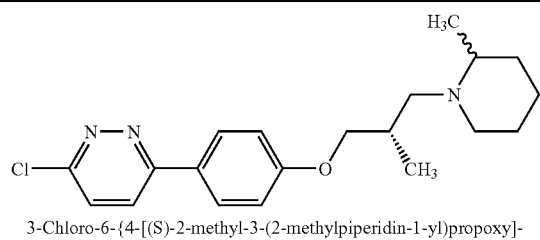<br>3-Chloro-6-{4-[(S)-2-methyl-3-(2-methylpiperidin-1-yl)propoxy]-phenyl}pyridazine | 108-110 | 7.969 | $^1$H NMR ($CDCl_3$) 1.04 (d, 3H, —$CH_3$), 3.09 (m, 2H, —$CH_2$—), 7.06 (d, 2H, Ar—H), 7.50 (d, 1H, C—H), 7.77 (d, 1H, C—H), 8.00 (d, 2H, Ar—H) |

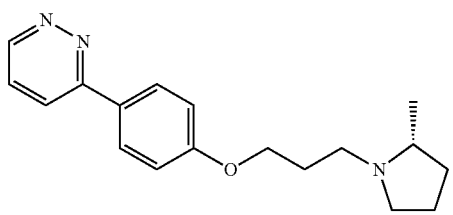

Example 45

3-{4-[3-((R)-2-Methyl-pyrrolidin-1-yl)-propoxy]-phenyl}-pyridazine

6-{4-[3-((R)-2-methyl-pyrrolidin-1-yl)propoxy]phenyl}pyridazine (R)-2-Methyl-1-{3-[4-(4,4,5,5-tetramethyl-[1,3,2]dioxaborolan-2-yl)-phenoxy]propyl}-pyrrolidine (1.1 g, 3.2 mmol), 3-chloropyridazine (0.485 g, 4.24 mmol) and tetrakis(triphenylphosphine)palladium(0) (0.258 g, 0.223 mmol), mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders (such as asthma), inflammation, and myocardial infarction. In certain embodiments, the compounds can be administered to treat narcolepsy or other sleep/wake disorders, such as obstructive sleep apnea/hypopnea syndrome, and shift work sleep disorder; obesity, cognition, attention deficit hyperactivity disorder (ADHD), and dementia. In other embodiments, the compounds can be administered to treat narcolepsy or other sleep/wake disorders, such as obstructive sleep apnea/hypopnea syndrome, and shift work sleep disorder; or they can used to treat obesity, or they can used to treat cognition, or they can used to treat attention deficit hyperactivity disorder (ADHD), or they can used to treat dementia.

Compounds of the invention either have demonstrated or are expected to demonstrate inhibition of $H_3$ and thereby for utility for treatment of the indications described herein. Such utilities can be determined using, for example, the following assays as set forth below. They are not intended, nor are they to be construed, as limiting the scope of the disclosure.

Rat H₃ Assays:

Cell line development and membrane preparation. The rat H₃ receptor cDNA was PCR amplified from reverse-transcribed RNA pooled from rat thalamus, hypothalamus, striatum and prefrontal cortex with a sequence corresponding to by #338-1672 of Genbank file #NM_053506, encoding the entire 445-amino-acid rat histamine H₃ receptor. This was engineered into the pIRES-neo3 mammalian expression vector, which was stably transfected into the CHO-A3 cell line (Euroscreen, Belgium), followed by clonal selection by limiting dilution. Cells were harvested and cell pellets were frozen (—80° C.). Cell pellets were resuspended in 5 mM Tris-HCl, pH 7.5 with 5 nM EDTA and a cocktail of protease inhibitors (Complete Protease Inhibitior Tablets, Roche Diagnostics). Cells were disrupted using a polytron cell homogenizer and the suspension was centrifuged at 1000×g for 10 minutes at 4° C. The pellet was discarded and the supernatant centrifuged at 40,000×g for 30 min at 4° C. This membrane pellet was washed in membrane buffer containing 50 mM Tris-HCl, pH 7.5 with 0.6 mM EDTA, 5 mM MgCl₂ and protease inhibitors, recentrifuged as above and the final pellet resuspended in membrane buffer plus 250 mM sucrose and frozen at –80° C.

Radioligand Binding. Membranes were resuspended in 50 mM Tris HCl (pH 7.4), 5 mM MgCl₂, 0.1% BSA. The membrane suspensions (10 μg protein per well) were incubated in a 96 well microtiter plate with [³H]-N-alpha-methylhistamine (approximately 1 nM final concentration), test compounds at various concentrations (0.01 nM-30 μM) and scintillation proximity beads (Perkin Elmer, FlashBlueGPCR Scintillating Beads) in a final volume of 80 μl for 4 hours at room temperature, protected from light. Non-specific binding was determined in the presence of 10 μM clobenpropit. Radioligand bound to receptor, and therefore in proximity to the scintillation beads, was measured using a MicroBeta scintillation counter.

GTPγS Binding. Membranes were resuspended in 20 mM HEPES pH 7.4 containing: 1 mM EDTA, 0.17 mg/ml dithiothreitol, 100 mM NaCl, 30 μg/ml saponin and 5 mM MgCl₂. For measurement of inverse agonist activity, increasing concentrations of test compounds were incubated in a 96 well microtiter plate with 10 μg/well membrane protein, 5 μM GDP, scintillation proximity beads (Perkin Elmer, FlashBlue-GPCR Scintillating Beads) and [³⁵S]-GTPγS (0.1 nM final concentration). Following incubation for 45 minutes in the dark at room temperature, the microtiter plate was centrifuged at 1000×g for 5 minutes and radioactivity bound to the membranes was counted using a MicroBeta scintillation counter. Non-specific binding was measured in the presence of 10 μM GTP. A decrease in bound [³⁵S]-GTPγS is indicative of H₃ receptor inverse agonist activity in this assay. Antagonist activity of test compounds was determined in a similar experiment under the following conditions. Membranes were resuspended in 20 mM HEPES pH 7.4 containing: 1 mM EDTA, 0.17 mg/ml dithiothreitol, 200 mM NaCl, 30 μg/ml saponin and 20 mM MgCl₂. The membranes were incubated at 10 μg/well membrane protein in a microtiter plate with increasing concentrations of test compounds, 20 μM GDP, scintillation proximity beads and [³⁵S]-GTPγS (0.1 nM final concentration) plus 30 nM R-alpha-methylhistamine. The microtiter plates were incubated and processed as described above. A decrease in R-alpha-methylhistamine stimulated [³⁵S]-GTPγS binding is indicative of H₃ receptor antagonist activity in this assay.

Human H₃ Assays:

Methods: CHO cells stably expressing the human H₃ receptor (GenBank: NM_007232) were harvested and cell pellets were frozen (—80° C.). Cell pellets were resuspended in 5 mM Tris-HCl, pH 7.5 with 5 nM EDTA and a cocktail of protease inhibitors (Complete Protease Inhibitior Tablets, Roche Diagnostics). Cells were disrupted using a polytron cell homogenizer and the suspension was centrifuged at 1000×g for 10 minutes at 4° C. The pellet was discarded and the supernatant centrifuged at 40,000×g for 30 min at 4° C. This membrane pellet was washed in membrane buffer containing 50 mM Tris-HCl, pH 7.5 with 0.6 mM EDTA, 5 mM MgCl₂ and protease inhibitors, recentrifuged as above and the final pellet resuspended in membrane buffer plus 250 mM sucrose and frozen at –80° C.

Radioligand Binding. Membranes were resuspended in 50 mM Tris HCl (pH 7.4), 5 mM MgCl₂, 0.1% BSA. The membrane suspensions (10 μg protein per well) were incubated in a 96 well microtiter plate with [³H]-N-alpha-methylhistamine (approximately 1 nM final concentration), test compounds at various concentrations (0.01 nM-30 μM) and scintillation proximity beads (Perkin Elmer, FlashBlueGPCR Scintillating Beads) in a final volume of 80 μl for 4 hours at room temperature, protected from light. Non-specific binding was determined in the presence of 10 μM clobenpropit. Radioligand bound to receptor, and therefore in proximity to the scintillation beads, was measured using a MicroBeta scintillation counter.

GTPγS Binding. Membranes were resuspended in 20 mM HEPES pH 7.4 containing: 1 mM EDTA, 0.17 mg/ml dithiothreitol, 100 mM NaCl, 30 μg/ml saponin and 5 mM MgCl₂. For measurement of inverse agonist activity, increasing concentrations of test compounds were incubated in a 96 well microtiter plate with 10 μg/well membrane protein, 5 μM GDP, scintillation proximity beads (Perkin Elmer, FlashBlue-GPCR Scintillating Beads) and [³⁵S]-GTPγS (0.1 nM final concentration). Following incubation for 45 minutes in the dark at room temperature, the microtiter plate was centrifuged at 1000×g for 5 minutes and radioactivity bound to the membranes was counted using a MicroBeta scintillation counter. Non-specific binding was measured in the presence of 10 μM GTP. A decrease in bound [³⁵S]-GTPγS is indicative of H₃ receptor inverse agonist activity in this assay. Antagonist activity of test compounds was determined in a similar experiment under the following conditions. Membranes were resuspended in 20 mM HEPES pH 7.4 containing: 1 mM EDTA, 0.17 mg/ml dithiothreitol, 200 mM NaCl, 30 μg/ml saponin and 20 mM MgCl₂. The membranes were incubated at 10 μg/well membrane protein in a microtiter plate with increasing concentrations of test compounds, 20 μM GDP, scintillation proximity beads and [³⁵S]-GTPγS (0.1 nM final concentration) plus 30 nM R-alpha-methylhistamine. The microtiter plates were incubated and processed as described above. A decrease in R-alpha-methylhistamine stimulated [³⁵S]-GTPγS binding is indicative of H₃ receptor antagonist activity in this assay.

Other assays that may be used in connection with the present invention are set forth below. Examples of the present invention can be tested in the following in vivo models:

Evaluation of Wake Promoting Activity in Rats

The methodology utilized for evaluating wake promoting activity of test compounds is based on that described by Edgar and Seidel, *Journal of Pharmacology and Experimental Therapeutics*, 283:757-769, 1997, and incorporated herein in its entirety by reference.

Compounds of the invention either have demonstrated or are expected to demonstrate utility for wake promoting activity.

Dipsogenia Model: Inhibition of histamine agonist-induced water drinking in the rat. Histamine, and the H₃-selective agonist (R)-α-methylhistamine (RAMH) induce water drinking behavior in the rat when administered either peripherally or centrally (Kraly, F. S., June, K. R. 1982 *Physiol. Behav.* 28: 841; Leibowitz, S. F. 1973 *Brain Res.* 63:440; Ligneau X., Lin, J-S., Vanni-Mercier G., Jouvet M., Muir J. L., Ganellin C. R., Stark H., Elz S., Schunack W., Schwartz, J-C. 1998 *J Pharmcol. Exp. Ther.* 287:658-66; Clapham, J. and Kilpatrick G. J. 1993 *Eur. J. Pharmacol.* 232:99-103) an effect which is blocked by H₃ receptor antagonists thioperamide and ciproxifan. Compounds of the invention either have demonstrated or are expected to block RAMH induce water drinking behavior. Novel object discrimination: Novel object discrimination (NOD; also referred to as novel object recognition) is an assay for short-term visual recognition memory that was first described by Ennaceur and Delacour (Ennaceur, A. and Delacour, J. (1988) *Behav Brain Res* 31: 47-59).

Social recognition: Social recognition (SR) is an assay for short-term social (olfactory) memory that was first described by Thor and Holloway (1982). Thor, D. and Holloway, W. (1982) *J Comp Physiolog Psychcol* 96: 1000-1006.

Compounds of the invention either have demonstrated or are expected to demonstrate inhibition of H₃ and thereby utility for treatment of the indications described herein.

Table B lists the Human binding data for Examples 1-45 of the present invention. Binding constants ($K_i$) for Examples 1-45 in the Human H₃ method described herein are expressed by letter descriptor to indicate the following ranges: "+++" is less than 50 nM; "++" is 51-100 nM; "+" is >101 nM.

TABLE B

| EXAMPLE NUMBER | HUMAN H₃ BINDING $K_i$ (nM) |
|---|---|
| 1 | +++ |
| 2 | +++ |
| 3 | +++ |
| 4 | +++ |
| 5 | +++ |
| 6 | +++ |
| 7 | +++ |
| 8 | +++ |
| 9 | +++ |
| 10 | + |
| 11 | + |
| 12 | +++ |
| 13 | +++ |
| 14 | + |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | +++ |
| 31 | ++ |
| 32 | +++ |
| 33 | +++ |
| 34 | +++ |
| 35 | +++ |

TABLE B-continued

| EXAMPLE NUMBER | HUMAN H₃ BINDING $K_i$ (nM) |
|---|---|
| 36 | +++ |
| 37 | +++ |
| 38 | +++ |
| 39 | +++ |
| 40 | +++ |
| 41 | +++ |
| 42 | +++ |
| 43 | +++ |
| 44 | + |
| 45 | +++ |

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed:

1. A compound of Formula I:

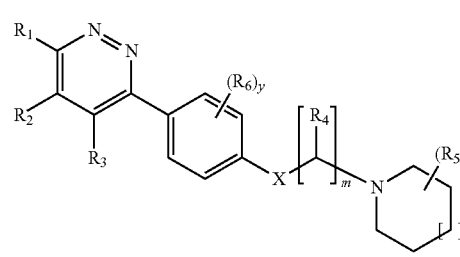

wherein:

$R^1$ is H, —OR⁷, —SR⁷, —SOR⁷, —SO₂R⁷, —NR⁹R¹⁰, halogen, $C_{1-4}$ alkyl, $C_{4-10}$ cycloalkyl, $C_{1-4}$ haloalkyl, $C_{6-12}$ aryl, 5-10 membered heteroaryl, or 3-10 membered heterocycloalkyl, wherein each of said $C_{1-4}$ alkyl, $C_{4-10}$ cycloalkyl, $C_{1-4}$ haloalkyl, $C_{6-12}$ aryl, 5-10 membered heteroaryl, and 3-10 membered heterocycloalkyl is optionally substituted by 1, 2, or 3 $R^{11}$;

$R^2$ and $R^3$ are independently H or $C_{1-4}$ alkyl; or $R^2$ and $R^3$ are taken together to form a $C_{4-10}$ cycloalkyl or phenyl, wherein each of said $C_{4-10}$ cycloalkyl and phenyl is optionally substituted by 1, 2, or 3 halogen or $C_{1-4}$ alkyl;

each $R^4$ is independently H or $C_{1-4}$ alkyl or OH;

each $R^5$ is independently $C_{1-4}$ alkyl, or hydroxyalkyl;

each $R^6$ is independently halogen, $C_{1-4}$ haloalkyl, —OH, $C_{1-4}$ alkyl, —O—$C_{1-4}$ alkyl, —NR⁹R¹⁰, or CN;

$R^7$ is $C_{1-4}$ alkyl, C4-10 cycloalkyl, 5-10 membered heteroaryl, $C_{6-12}$ aryl, $C_{6-12}$ aryl$C_{1-6}$alkyl, 5-10 membered heteroarylalkyl, or a 3-10 membered heterocycloalkyl;

$R^9$ and $R^{10}$ are independently H, $C_{1-4}$ alkyl, or arylalkyl;

each $R^{11}$ is halogen, —OH, —OC$_{1-4}$ alkyl, $C_{1-4}$ alkyl, $C_{1-4}$ haloalkyl, or —CN;

X is O or S;

m is 2, 3, 4, 5, or 6;

n is 0, 1, or 2;

y is 0, 1, 2, 3, or 4;

z is 0, 1, 2, 3, or 4;

or a stereoisomer or a pharmaceutically acceptable salt thereof.

2. A compound according to claim 1, wherein $R^1$ is selected from the group consisting of H, —$OR^7$, —$SR^7$, —$SOR^7$, —$SO_2R^7$, —$NR^9R^{10}$, halogen, $C_{1-4}$ alkyl, $C_{1-4}$ haloalkyl, aryl and heteroaryl.

3. A compound according to claim 1, wherein $R^1$ is halogen, $C_{1-4}$ alkyl, aryl, heteroaryl, heterocycloalkyl, or —$NR^9R^{10}$.

4. A compound according to claim 1, wherein $R^1$ is H, halogen, or —$NH_2$.

5. A compound according to claim 1, wherein $R^1$ is chloride or fluoride.

6. A compound according to claim 1, wherein $R^1$ is $OR^7$.

7. A compound according to claim 1, wherein $R^1$ is —$SR^7$, —$SOR^7$, or —$SO_2R^7$.

8. A compound according to claim 1, wherein $R^1$ is H, methyl, phenyl, pyrrolidinyl, piperidinyl, morpholinyl, thiophenyl, pyridinyl, —$OC_{1-4}$alkyl, —Oaryl, —$OCH_2$aryl, —$SC_{1-4}$alkyl, —$SCH_2$aryl, —$SOCH_2$aryl, —$SO_2CH_2$aryl, or benzofuranyl.

9. A compound according to claim 1, wherein $R^1$ is H.

10. A compound according to claim 1, wherein $R^5$ is $C_{1-4}$ alkyl and n is 0.

11. A compound according to claim 1, wherein $R^2$ is H.

12. A compound according to claim 1, wherein $R^3$ is H.

13. A compound according to claim 1, wherein $R^2$, $R^3$, $R^4$ and $R^6$ are each H.

14. A compound according to claim 1, wherein $R^2$ and $R^3$ are each H.

15. A compound according to claim 1, wherein $R^2$ and $R^3$ are taken together to form a $C_{4-10}$ cycloalkyl.

16. A compound according to claim 1, wherein $R^2$ and $R^3$ are taken together to form a phenyl.

17. A compound according to claim 1, wherein each $R^4$ is independently H or methyl.

18. A compound according to claim 1, wherein $R^4$ is H.

19. A compound according to claim 1, wherein each $R^5$ is methyl.

20. A compound according to claim 1, wherein each $R^6$ is independently $C_{1-4}$alkyl.

21. A compound according to claim 1, wherein m is 2 or 3.

22. A compound according to claim 1, wherein m is 3.

23. A compound according to claim 1, wherein n is 0 or 1.

24. A compound according to claim 1, wherein n is 0.

25. A compound according to claim 1, wherein y is 0.

26. A compound according to claim 1, wherein z is 1.

27. A compound according to claim 1, wherein X is O.

28. The compound according to claim 1 selected from the group consisting of:
3-Chloro-6-{4-[3-((R)-2-methylpyrrolidin1-yl)propoxy]phenyl}pyridazine;
3-Chloro-6-[4-(3-piperidin-1-yl-propoxy)-phenyl]pyridazine;
3-Methyl-6-{4-[3-((R)-2-methyl-pyrrolidin-1-yl)-propoxy]-phenyl}pyridazine;
3-{4-[3-((R)-2-Methyl-pyrrolidin-1-yl)-propoxy]-phenyl}-6-phenylpyridazine;
3-{4-[3-((R)-2-Methyl-pyrrolidin-1-yl)-propoxy]-phenyl}-6-pyrrolidin-1-yl-pyridazine;
4-(6-{4-[3-((R)-2-Methylpyrrolidin-1-yl)-propoxy]phenyl}pyridazin-3-yl)morpholine;
6-{4-[3-((R)-2-Methyl-pyrrolidin-1-yl)-propoxy]-phenyl}pyridazin-3-ylamine;
Methyl-(6-{4-[3-((R)-2-methyl-pyrrolidin-1-yl)-propoxy]phenyl}pyridazin-3-yl)amine;
1-(6-{4-[3-((R)-2-Methylpyrrolidin-1-yl)-propoxy]phenyl}pyridazin-3-yl)piperidin-4-ol;
3-Chloro-6-{3-methoxy-4-[3-((R)-2-methyl-pyrrolidin-1-yl)propoxy}phenyl}pyridazine;
3-Chloro-6-[3-methoxy-4-(3-piperidin-1-yl-propoxy)phenyl]pyridazine;
3-Chloro-6-[2-methyl-4-(3-piperidin-1-yl-propoxy)phenyl]pyridazine;
5-(6-Chloro-pyridazin-3-yl)-2-[3-((R)-2-methyl-pyrrolidin-1-yl)-propoxy]benzonitrile;
5-(6-Chloro-pyridazin-3-yl)-2-(3-piperidin-1-yl-propoxy)benzonitrile;
1-Chloro-4-[4-(3-piperidin-1-yl-propoxy)-phenyl]-6,7-dihydro-5H-cyclopenta[d]pyridazine;
3-{4-[3-((R)-2-Methyl-pyrrolidin-1-yl)-propoxy]phenyl}-6-thiophen-2-yl-pyridazine;
1-Chloro-4-{4-[3-((R)-2-metyl-pyrrolidin-1-yl)-propoxy]-phenyl}-6,7-dihydro-5H-cyclopenta[d]pyridazine;
3-Chloro-6-{4-[3-((R)-2-methyl-pyrrolidin-1-yl)-propoxy]-phenyl}-4,5-diaza-tricyclo[6.2.2.0*2,7*]dodeca-2(7),3,5-triene;
3-(5-Chloro-pyridin-3-yloxy)-6-{4-[3-((R)-2-methyl-pyrrolidin-1-yl)-propoxyphenyl}pyridazine;
3-Benzyloxy-6-[4-(3-piperidin-1-yl-propoxy)phenyl]pyridazine;
3-Benzyloxy-6-{4-[3-((R)-2-methyl-pyrrolidin-1-yl)-propoxy]phenyl}pyridazine;
3-Methoxy-6-{4-[3-((R)-2-methyl-pyrrolidin-1-yl-propoxy]-phenyl}pyridazine;
3-Methoxy-6-{4-3-piperidin-1-yl-propoxy)-phenyl]pyridazine;
3-Isopropoxy-6-{4-[3-((R)-2-methyl-pyrrolidin-1-yl)-propoxy]phenylpyridazine;
3-Phenoxy-6-[4-(3-piperidin-1-yl-propoxy)phenyl]pyridazine;
3-(4-Fluoro-benzyloxy)-6-{4-[3-((R)-2methyl-pyrrolidin-1-yl)-propoxy]phenyl}pyridazine;
3-{4-[3-((R)-2-Methyl-pyrrolidin-1-yl)-propoxy]-phenyl}-6-(4-trifluoromethyl-benzyloxy)pyridazine;
Ethyl-(6-{4-[3-((R)-2-methyl-pyrrolidin-1-yl)-propoxy]-phenyl}pyridazin-3-yl)amine;
Benzyl-(6-{4-[3-((R)-2-methyl-pyrrolidin-1-yl)-propoxy]-phenyl}-pyridazin-3-yl)amine;
3-{4-[3-((R)-2-Methyl-pyrrolidin-1-yl-propoxy]-phenyl}-6-methylsulfanylpyridazine;
3-Methylsulfanyl-6-[4-(3-piperidin-1-yl-propoxy)phenyl]pyridazine;
1-{4-[3-((R)-2-Methyl-pyrrolodin-1-yl)-propoxy]-phenyl}-4-methylsulfanyl-6,7-dihydro-5H-cyclopenta[d]pyridazine;
3-Benzylsulfanyl-6-{4-[3-((R)-2-methyl-pyrrolidin-1-yl)-propoxy]phenyl}pyridazine;
3-Benzylsulfanyl-6-[4-(3-piperidin-1-yl-propoxy)-phenyl]pyridazine;
3-{4-[3-((R)-2-Methyl-pyrrolidin-1-yl)-propoxy]-phenyl}-6-phenylmethanesulfinyl-pyridazine;
3-Phenylmethanesulfinyl-6-[4-(3-piperidin-1-yl-propoxy)phenyl]pyridazine;
3-{4-[3-((R)-2-Methyl-pyrrolidin-1-yl)-propoxy]-phenyl}-6-phenylmethanesulfonyl-pyridazine;
3-Phenylmethanesulfonyl-6-[4-(3-piperidin-1-yl-propoxy)phenyl]pyridazine;
1-Methoxy-4-{4-[3-((R)-2-methylpyrrolidin-1-yl)-propoxy]-phenyl}6,7-dihydro-5H-cyclopenta[d]pyridazine;

1-Methoxy-4-{4-[3-((R)-2-methyl-pyrrolidin-1-yl-propoxy]-phenyl}phthalazine;

3-Benzofuran-2-yl-6-{4-[3-((R)-2-methyl-pyrrolidin-1-yl)-propoxy]-phenyl}pyridazine;

1-Benzylsulfanyl-4-{4-[3-((R)-2-methyl-pyrrolidin-1-yl)propoxy]-phenyl}-6,7-dihydro-5H-cyclopenta[d]pyridazine;

3-Chloro-6-{4-[(S)-2-methyl-3-((R)-2-methylpyrrolidin-1-yl)-propoxy]phenyl}pyridazine;

3-Chloro-6-{4-[(S)-2-methyl-3-(2-methylpiperidin-1-yl)propoxy]-phenyl}pyridazine; and 6-{4-[3-((R)-2-methyl-pyrrolidin-1-yl)propoxy]phenyl}pyridazine;

or a stereoisomer or a pharmaceutically acceptable salt thereof.

29. A pharmaceutical composition, comprising:
at least one compound according to claim 1 or a stereoisomer or a pharmaceutically acceptable salt thereof, and at least one pharmaceutically acceptable carrier or diluent.

30. A pharmaceutical composition according to claim 29, further comprising at least one additional therapeutic agent.

* * * * *